(12) United States Patent
Hamilton et al.

(10) Patent No.: US 12,064,550 B2
(45) Date of Patent: Aug. 20, 2024

(54) INTEGRATED SENSOR ASSEMBLY OF A RESPIRATORY THERAPY SYSTEM

(71) Applicant: Fisher & Paykel Healthcare Limited, Auckland (NZ)

(72) Inventors: Mark Samuel Hamilton, Auckland (NZ); Alan John Grimmer, Auckland (NZ); Donald Roy Kuriger, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 462 days.

(21) Appl. No.: 17/453,770

(22) Filed: Nov. 5, 2021

(65) Prior Publication Data

US 2022/0126041 A1 Apr. 28, 2022

Related U.S. Application Data

(63) Continuation of application No. 16/333,342, filed as application No. PCT/NZ2017/050129 on Oct. 9, 2017, now Pat. No. 11,197,970.

(Continued)

(51) Int. Cl.
*A61M 16/00* (2006.01)
*A61M 16/10* (2006.01)
(Continued)

(52) U.S. Cl.
CPC .... *A61M 16/0066* (2013.01); *A61M 16/0069* (2014.02); *A61M 16/024* (2017.08);
(Continued)

(58) Field of Classification Search
CPC .............. A61M 16/00; A61M 16/0003; A61M 16/0066; A61M 16/0069; A61M 16/022;
(Continued)

(56) References Cited

U.S. PATENT DOCUMENTS 4,765,326 A * 8/1988 Pieper .................. A62B 18/006
128/202.22
4,971,052 A 11/1990 Edwards
(Continued)

FOREIGN PATENT DOCUMENTS

AU 2015203636 B2 7/1989
EP 0352938 A2 7/1989
(Continued)

OTHER PUBLICATIONS

International Search Report mailed Jan. 30, 2018, issued in corresponding PCT/NZ2017/050129.

*Primary Examiner* — Joseph D. Boecker
(74) *Attorney, Agent, or Firm* — Knobbe, Martens, Olson & Bear, LLP

(57) ABSTRACT

A flow generator 21 for a respiratory therapy system configured to deliver a breathable gas flow to a patient comprises a housing 27 comprising an inlet 28 and an outlet 25 and a gas flow path between the inlet 28 and outlet 25. An impeller is mounted within the housing 27 for rotation about an axis, the impeller configured to be rotationally driven by a motor to provide a gas flow along the gas flow path. Various embodiments are disclosed in which the flow generator 21 further comprises a sensor 23 mounted in the housing 27 in the gas flow path and configured to detect a property of the gas flow. The sensor 23 may be mounted in the outlet 25 so as to project into the gas flow path. Flow generator may comprise an axial inlet 28 and a tangential outlet 25. In another embodiment the sensor 23 may be mounted in the inlet 28.

18 Claims, 15 Drawing Sheets

Related U.S. Application Data

(60) Provisional application No. 62/406,730, filed on Oct. 11, 2016.

(51) Int. Cl.
  *A61M 16/16* (2006.01)
  *F04D 25/06* (2006.01)
  *G01F 1/36* (2006.01)
  *G01F 1/46* (2006.01)

(52) U.S. Cl.
  CPC .......... *A61M 16/109* (2014.02); *A61M 16/16* (2013.01); *F04D 25/0666* (2013.01); *G01F 1/363* (2013.01); *G01F 1/46* (2013.01); *A61M 2016/0027* (2013.01); *A61M 2016/0033* (2013.01); *A61M 2016/0039* (2013.01); *A61M 2205/502* (2013.01); *A61M 2205/52* (2013.01)

(58) Field of Classification Search
  CPC .. A61M 16/024; A61M 16/109; A61M 16/16; A61M 2016/0027; A61M 2016/0033; A61M 2016/0039; F04D 25/0666; F04D 17/16; G01F 1/363; G01F 1/46
  See application file for complete search history.

(56) References Cited

U.S. PATENT DOCUMENTS

| | | | |
|---|---|---|---|
| 6,237,592 B1 | 5/2001 | Srjadi et al. | |
| 6,603,273 B1 | 8/2003 | Wickham et al. | |
| 7,607,360 B2 | 10/2009 | Todokoro et al. | |
| 11,197,970 B2 | 12/2021 | Hamilton et al. | |
| 2004/0112381 A1 | 6/2004 | Ujhazy et al. | |
| 2005/0103339 A1 | 5/2005 | Daly et al. | |
| 2006/0283450 A1 | 12/2006 | Shissler et al. | |
| 2009/0241943 A1 | 10/2009 | Schwank et al. | |
| 2011/0120462 A1 | 5/2011 | Tatkov et al. | |
| 2011/0126832 A1 | 6/2011 | Winter et al. | |
| 2011/0217182 A1 | 9/2011 | Hanewald | |
| 2012/0114512 A1 | 5/2012 | Lofy et al. | |
| 2012/0138051 A1 | 6/2012 | Curran et al. | |
| 2012/0138058 A1* | 6/2012 | Fu ................... A61M 16/0066 128/204.23 |
| 2013/0133656 A1 | 5/2013 | Nightingale et al. | |
| 2014/0000610 A1 | 1/2014 | Rapoport et al. | |
| 2015/0165140 A1 | 6/2015 | Cappelli et al. | |
| 2015/0320949 A1 | 11/2015 | Jaffe | |
| 2016/0243325 A1 | 8/2016 | Bowman et al. | |
| 2016/0279378 A1 | 9/2016 | Cipollone et al. | |
| 2016/0375209 A1 | 12/2016 | Shadie et al. | |
| 2017/0074695 A1* | 3/2017 | Baecke ............... G01L 19/0038 |
| 2018/0110946 A1 | 4/2018 | Fuste | |
| 2019/0054265 A1 | 2/2019 | Shahar et al. | |

FOREIGN PATENT DOCUMENTS

| | | |
|---|---|---|
| EP | 2017586 A1 | 1/2009 |
| WO | WO 2012/075433 A2 | 6/2012 |
| WO | WO 2012/135912 A1 | 10/2012 |
| WO | WO 2014/000039 A1 | 1/2014 |
| WO | WO 2014/041472 A1 | 3/2014 |
| WO | WO 2016/036260 A1 | 3/2016 |

\* cited by examiner

INTEGRATED SENSOR ASSEMBLY OF A RESPIRATORY THERAPY SYSTEM

INCORPORATION BY REFERENCE TO ANY PRIORITY APPLICATIONS

The present application is a continuation application of U.S. patent application Ser. No. 16/333,342, filed on Mar. 14, 2019, which is a 371 of International PCT/NZ2017/050129, filed Oct. 9, 2017, which claims priority benefit of U.S. Provisional Application Ser. No. 62/406,730, filed on Oct. 11, 2016, the disclosures of each of which are hereby incorporated by reference in their entireties.

BACKGROUND OF THE DISCLOSURE

Field of the Disclosure

The present disclosure generally relates to an integrated sensor of a respiratory therapy system, and in embodiments relates to a flow generator, a sensor and a respiratory therapy system, for delivering breathable gases to a patient. This application claims priority from provisional application U.S. 62/406,730 filed on 11 Oct. 2016, the entire contents of which are hereby incorporated by reference.

Description of the Related Art

One example of use of a respiratory therapy system is for the treatment of obstructive sleep apnea (OSA) by continuous positive airway pressure (CPAP) or Bi-level (BIPAP) flow generator systems involves the continuous delivery of pressurized gases to the air-ways of a human via a gas delivery conduit and a patient interface. Typically the patient interface creates at least a substantial seal on or around the nose and/or the mouth.

Other examples of use of a respiratory therapy system is for nasal high flow therapy (NHF) whereby a high flow of breathable gases is delivered to the patient by a non-sealing patient interface such as non-sealing nasal prongs received in the nares of the patient.

Some such respiratory therapy systems incorporate a flow generator which typically comprises an impeller driven by a motor. Rotation of the impeller by the motor generates a breathable gas flow which is driven from the flow generator to the patient via a breathing gas delivery circuit, typically a combination of one or more gas delivery conduits, one or more conduit connectors, and a patient interface. The flow generator may be integrated with other parts of the respiratory therapy system such as a controller and a humidifier which humidifies the breathable gas flow prior to delivery to the patient. In other examples, the flow generator is a separate component which may have a dedicated controller, and be connected to other components of the respiratory therapy system by suitable conduits and conduit connectors.

It is important to be able control the flow and/or pressure of the breathable gas flow so as to achieve the desired therapy for the patient. To this end it is known to provide one or more sensors in the gas delivery path, the output from which is processed by a controller to vary the flow and/or pressure of the breathable gas flow. Such sensors can comprise flow sensors or pressure sensors or any combination of such sensors. In one example, a sensor is provided which measures and generates a signal indicative of the dynamic pressure of breathable gas through some part of the system. This dynamic pressure signal is processed to generate an output which may be used to determine the pressure and/or flow rate of the gas in the system (or in part of the system). In some cases other sensors such as humidity sensors can also be provided.

In any respiratory therapy system, ease of manufacture, assembly, maintenance, cleaning and use can all be important factors. It is desirable to be able to provide a system which improves any one or more of these factors.

SUMMARY OF THE DISCLOSURE

The present disclosure provides a flow generator, flow sensor, and a respiratory therapy system, any and each of which can be used with any type of respiratory therapy whereby a flow of breathable gas is generated by a flow generator and delivered to a patient.

It is an object of the present disclosure to provide an improved flow generator, and/or a flow sensor and/or a respiratory therapy system, and/or that will at least provide the public or the medical profession with a useful choice.

According to a first aspect of the invention there is provided a flow generator for a respiratory therapy system configured to deliver a breathable gas flow to a patient, the flow generator comprising:
  a housing comprising an inlet and an outlet and a gas flow path between the inlet and outlet;
  an impeller mounted within the housing for rotation about an axis, the impeller configured to be rotationally driven by a motor to provide a gas flow along the gas flow path;
  the flow generator further comprising a sensor mounted in the housing in the gas flow path and configured to detect a property of the gas flow.

The sensor may be configured to detect differential pressure in the gas flow path.

The sensor may be a flow sensor configured to generate a signal indicative of flow rate of the gas flow, from the detected differential pressure. The sensor may be a pressure sensor configured to generate a signal indicative of the pressure of the gas flow, from the detected differential pressure.

The sensor preferably comprises first and second sensor openings, the sensor being mounted in the housing such that the first sensor opening faces towards the direction of gas flow through the gas flow path, and the second sensor opening faces away from the direction of gas flow through the gas flow path.

The flow generator may be a centrifugal flow generator.

The sensor may be mounted in either the inlet or the outlet of the housing. The outlet may be a radial or tangential outlet configured to deliver the gas flow from the housing in a direction substantially perpendicular to the axis; the sensor being mounted in the radial or tangential outlet. In a preferred embodiment the outlet is a tangential outlet. The tangential outlet preferably comprises opposed radially inner and outer side walls, the sensor being mounted on the radially outer side wall. The inlet may be an axial inlet configured to deliver gas into the housing in a direction substantially parallel to the axis, the sensor being mounted in the axial inlet.

The sensor may comprise first and second sensor openings, the sensor being mounted in the housing such that the first sensor opening faces towards the direction of gas flow through the gas flow path, and the second sensor opening faces away from the direction of gas flow through the gas flow path, wherein the first and sensor openings are spaced from the axis by a different amount.

In some embodiments, the first and second sensor openings are in fluid communication with the inlet via respective connecting tubes. The respective connecting tubes extend substantially parallel to the axis, into the gas flow path.

The sensor may be mounted in a middle third of the gas flow path when viewed along the axis of the gas flow path, that is, in the direction of gas flow.

The sensor may project into the gas flow path by a predetermined amount. The sensor may project across less than half the width of the gas flow path and in one example, projects across less than a third of the gas flow path.

The flow generator may comprise a motor, the motor being coupled with the impeller to rotationally drive the impeller within the housing.

The flow generator may comprise a controller, the controller being configured to receive an output from the sensor indicative of the gas flow in the gas flow path, and being further configured to control the rotational speed and/or torque of the impeller in dependence upon the output from the sensor.

According to another aspect of the invention there is provided a flow generator for a respiratory therapy system configured to deliver a breathable gas flow to a patient, the flow generator comprising:
 a housing comprising an inlet and an outlet and a gas flow path between the inlet and outlet;
 an impeller mounted within the housing for rotation about an axis, the impeller configured to be rotationally driven by a motor to provide a gas flow along the gas flow path;
 wherein the outlet is a radial or tangential outlet configured to deliver the gas flow from the housing in a direction substantially perpendicular to the axis;
 the flow generator further comprising a sensor mounted in the outlet of the housing in the gas flow path.

According to a further aspect of the invention there is provided a flow generator for a respiratory therapy system configured to deliver a breathable gas flow to a patient, the flow generator comprising:
 a housing comprising an inlet and an outlet and a gas flow path between the inlet and outlet;
 an impeller mounted within the housing for rotation about an axis, the impeller configured to be rotationally driven by a motor to provide a gas flow along the gas flow path;
 wherein the inlet is an axial inlet configured to deliver gas into the housing in a direction substantially parallel to the axis;
 the flow generator further comprising a sensor mounted in the axial inlet of the housing in the gas flow path.

According to another aspect of the invention there is provided a respiratory therapy system comprising the flow generator of any of the above aspects of the invention.

According to a further aspect of the invention there is provided a sensor for a respiratory therapy system configured to deliver a breathable gas flow to a patient along a gas flow path, the sensor comprising:
 a sensor body having a longitudinal axis;
 first and second sensor openings provided in the body, the sensor being configured to be mounted in the respiratory therapy system such that the first sensor opening faces towards the direction of gas flow through the gas flow path, and the second sensor opening faces away from the direction of gas flow through the gas flow path; wherein
 the sensor body comprising at least an oval/elliptical portion when viewed along the longitudinal axis, the oval portion being configured to be located in the gas flow path, the first and second sensor openings provided in the oval portion, and opposed across the oval portion in a direction substantially perpendicular to the longitudinal axis.

The oval portion may have a longer length and shorter width when viewed along the longitudinal axis, the first and second sensor opening being opposed across the longer length of the oval portion.

The ratio of the longer length to the shorter width of the oval portion may be substantially 2:1.

The sensor may comprise a base, the oval portion upstanding from the base, the base being configured to be located outside of the gas flow path when the oval portion is located in the gas flow path. The base may be substantially oblong when viewed along the longitudinal axis.

The sensor may further comprise an intermediate portion between the base and the oval portion, the intermediate portion being configured to be located in a wall defining the gas flow path, when the oval portion is located in the gas flow path. The intermediate portion may be substantially circular, when viewed along the longitudinal axis.

The sensor may comprise a pair of internal sensor flow paths each extending from a respective sensor opening in a direction substantially parallel to the longitudinal axis through the flow sensor, each sensor flow path being configured to communicate with a flow transducer, the flow transducer being operative to generate a signal indicative of the flow of gas in the gas flow path, from gas entering the sensor through the sensor openings.

Each sensor flow path may comprise a portion having parallel walls, when the sensor is viewed from the side. Each sensor flow path may comprise a portion having inclined walls, when the sensor is viewed from the side. Each sensor flow path may comprise a portion having outwardly flared walls, when the sensor is viewed from the side, the outwardly flared walls being configured to be located adjacent the flow transducer. Each sensor opening may be recessed from an outer wall of the oval portion.

According to another aspect of the invention there is provided a respiratory therapy system comprising the sensor of the above aspect of the invention.

According to another aspect of the invention there is provided a respiratory therapy system configured to deliver a breathable gas flow to a patient, comprising a flow generator and a controller, the flow generator comprising:
 a housing comprising an inlet and an outlet and a gas flow path between the inlet and outlet;
 an impeller mounted within the housing for rotation about an axis, the impeller configured to be rotationally driven by a motor to provide a gas flow along the gas flow path;
 the flow generator further comprising a sensor mounted in the housing in the gas flow path; the sensor comprising first and second sensor openings and being configured to generate an output signal;
 the controller being configured to:
 control the rotational speed and/or torque of the impeller to provide the breathable gas flow with a selected characteristic, wherein the selected characteristic results in a corresponding breathable gas pressure of the breathable gas being provided in the gas flow path; wherein the controller is operative according to:
 a first process step wherein the output from the sensor is used to generate a signal indicative of differential pressure between the first and second sensor openings in the gas flow path, and a subsequent process step wherein the signal indicative of differential pressure is used by the controller to generate a flow rate signal indicative of the flow rate of the breathable gas flow;

wherein the flow rate signal of the subsequent process step is generated in dependence upon a pre-determined indication of the variance of the relationship between differential pressure and flow rate of the breathable gas flow at a plurality of discrete, different, breathable gas pressures, such that the flow rate signal that is generated varies in dependence upon the breathable gas pressure which corresponds to the selected characteristic of the breathable gas flow.

The selected characteristic of the breathable gas flow may be the pressure or the flow rate of the breathable gas flow. The flow rate may be one of:

volumetric flow rate; or mass flow rate.

The controller is preferably configured to compare the breathable gas pressure corresponding to the selected characteristic with the plurality of discrete, different, breathable gas pressures for which there is the pre-determined indication of the variance of the relationship between differential pressure and flow rate of the breathable gas flow to match the corresponding breathable gas pressure with one of the plurality of discrete, breathable gas pressures, and to subsequently generate the flow rate signal with reference to the predetermined relationship between differential pressure and flow rate for the matched pressure.

The controller is preferably further configured if as a result of the comparison, the corresponding breathable gas pressure does not correspond to one of the plurality of discrete, breathable gas pressures, to generate the flow rate signal in dependence upon a signal indicative of an interpolation between the known predetermined relationship between differential pressure and flow rate for discrete breathable gas pressures above and below the selected breathable gas pressure.

The signal indicative of the interpolation is preferably generated as a result of a calculation by the controller, the calculation being any one or more of:

a) a line of best fit;
b) a logarithmic function;
c) an exponential function;
d) a polynomial function.

Alternatively, the signal indicative of the interpolation may be generated as a result of a calculation by the controller referencing a look-up table.

The selected characteristic may be selected by a clinician via an interface of the controller, and/or may be automatically selected by the controller.

The system may further comprise, or be in communication with, a memory configured to store any of the data required by the controller to generate the signals. The controller may comprise the memory, and/or the memory may be remote from the controller and on a remote controller or server for example.

The system of any of the above aspects of the invention may further comprise any one or more of:

a. a breathing gas humidifier;
b. a gas delivery conduit, which may or may not be heated; and/or
c. a patient interface.

At least one pressure sensor may be provided and configured to generate a signal indicative of the breathable gas pressure, the pressure sensor being located in any of the following locations:

a. at or in the housing of the flow generator;
b. at or in the gas delivery conduit.
c. at or in the patient interface;
d. between the flow generator and the breathing gas humidifier;
e. between the flow generator and the patient interface;

A plurality of pressure sensors may be provided, each pressure sensor being located in a different part of the system.

The patient interface may comprise any one of:

a) a full face mask comprising a mask frame and a cushion configured to seal around the patient's nose and mouth;
b) an oral mask comprising a mask frame and a cushion configured to seal around the patient's mouth;
c) a nasal mask comprising a mask frame and a cushion configured to seal around the patient's nose;
d) a nasal cannula having one or more prongs for insertion into the patient's nares;
e) a nasal mask comprising one or more nasal pillows configured to seal against the patient's nose; and
f) a hybrid mask comprising a combination of nasal pillows/prongs and an oral seal.
g) an endotracheal conduit; and
h) a tracheostomy interface.

Further aspects of the invention, which should be considered in all its novel aspects, will become apparent from the following description.

DESCRIPTION OF THE DRAWINGS

A number of embodiments of the disclosure will now be described by way of example with reference to the drawings in which.

DETAILED DESCRIPTION

Respiratory Therapy System

Figure 1A:
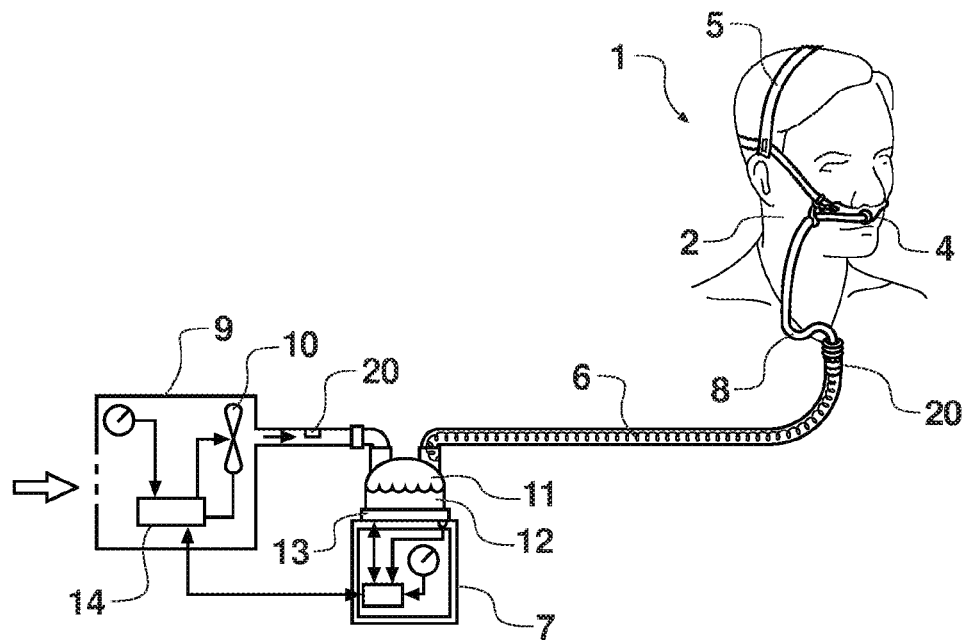
FIG. 1a is a schematic view of a first respiratory therapy system incorporating one or more aspects of the current disclosure.

With reference initially to FIG. 1A, a respiratory therapy system 1 as may comprise, or be used with, aspects of the present invention is shown. In such a system 1, a patient 2 is supplied with a humidified flow of gases through a patient interface 4. The patient interface 4 is retained in an operational position upon the patient's face using associated headgear 5. The interface 4 is connected to a humidified gases transportation pathway or inspiratory conduit 6. The inspiratory conduit 6 is connected at one end (either directly or indirectly) to the patient interface 4 and at an opposing end to the outlet of a humidifier 7. In other examples, a humidifier is not provided. In one embodiment the inspiratory conduit 6 is connected to the patient interface 4 via an extension tube/conduit 8. The humidifier 7 receives and humidifies gas supplied from a flow generator 9 which includes a rotationally driven impeller 10. The humidifier 7 may comprise a humidification chamber 11 filled with a humidification fluid such as water 12 and a heating means 13 for heating the water to humidify the gas path through the humidifier 7. A controller 14 may be provided to control and possibly vary one or more properties of the supplied gas, including but not limited to any one or more of: the pressure profile of the gas, the flow rate profiles of the gas at the patient interface 4, the temperature of the gas and/or the humidity of the gas. One or more pressure sensors 20 may be provided at any suitable position along the gas flow path of system 1, to generate a signal indicative of the breathable gas pressure of the gas flow at that point of the gas flow path of the system 1.

It will be appreciated that the control capabilities are dependent on the purpose and application of the respiratory system 1. The system 1 may therefore be controlled to provide breathable gas to the patient at a given pressure, or at a given flow rate. For example, in the application of in-hospital respiratory care, the flow rate of supplied gas may be monitored and controlled according to the patient's requirements but the pressure of the supplied gas is not necessarily monitored and controlled. In alternative embodiments, such as the use of the invention in a CPAP, the pressure profile of the supplied gas may be monitored and controlled.

For example, the respiratory therapy system 1 can be used for administering continuous positive airway pressure ("CPAP") treatments, variable positive airway pressure ("VPAP") treatments and/or bi-level positive airway pressure ("BiPAP") treatments.

Figure 1B:
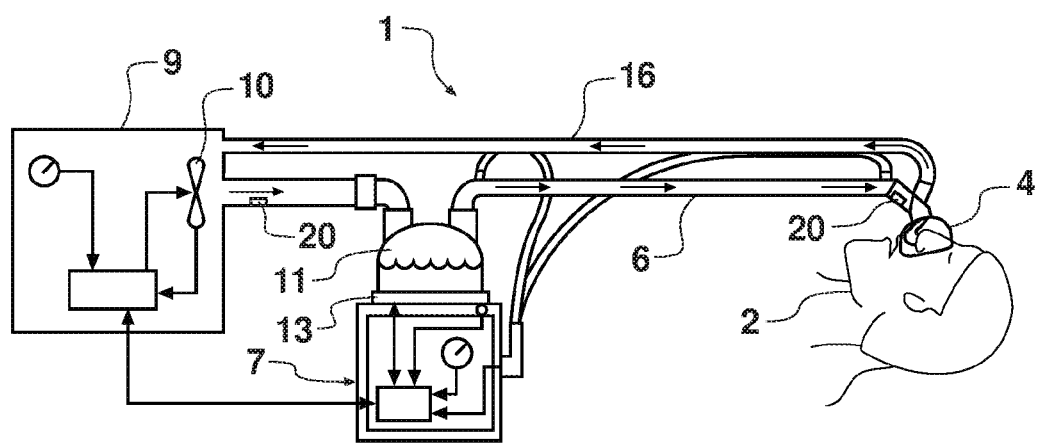
FIG. 1b is a schematic view of a second respiratory therapy system incorporating one or more aspects of the current disclosure.

With reference to FIG. 1B, a respiratory therapy system comprising a humidified ventilation system 1 is shown in which a patient 2 is receiving humidified and pressurised gases through a patient interface 4 connected to a humidified gases transportation pathway or inspiratory breathing conduit 6.

It will be appreciated the patient interface 4 may comprise any one of:
 a) a full face mask comprising a mask frame and a cushion configured to seal around the patient's nose and mouth;
 b) an oral mask comprising a mask frame and a cushion configured to seal around the patient's mouth;
 c) a nasal mask comprising a mask frame and a cushion configured to seal around the patient's nose;
 d) a nasal cannula having one or more prongs for insertion into the patient's nares;
 e) a nasal mask comprising one or more nasal pillows configured to seal against the patient's nose; and
 f) a hybrid mask comprising a combination of nasal pillows/prongs and an oral seal.
 g) an endotracheal conduit; and
 h) a tracheostomy interface.

Likewise the therapy delivery by the system 1 could also be continuous, variable or bi-level positive airway pressure or numerous other forms of respiratory therapy.

The inspiratory conduit 6 is connected to the outlet of a humidification chamber 11 which contains a volume of water 12. The inspiratory conduit 6 may include a heater or heater wires (not shown) which heat the humidified gases within the conduit 6, for example, to reduce the formation of condensation. The humidification chamber 11 is heated by a heater plate 13 of a humidifier base 7

A flow of gases (for example, air) is provided from flow generator 9, which enters the chamber 11. Exhaled gases from the patient's mouth are returned to the flow generator 9 via a return expiratory breathing conduit 16 that may also include a heater or heater wires (not shown), which heat the humidified gases within the expiratory breathing conduit 16, for example to reduce the formation of condensation.

Flow Generator with Integrated Sensor

Figure 2:
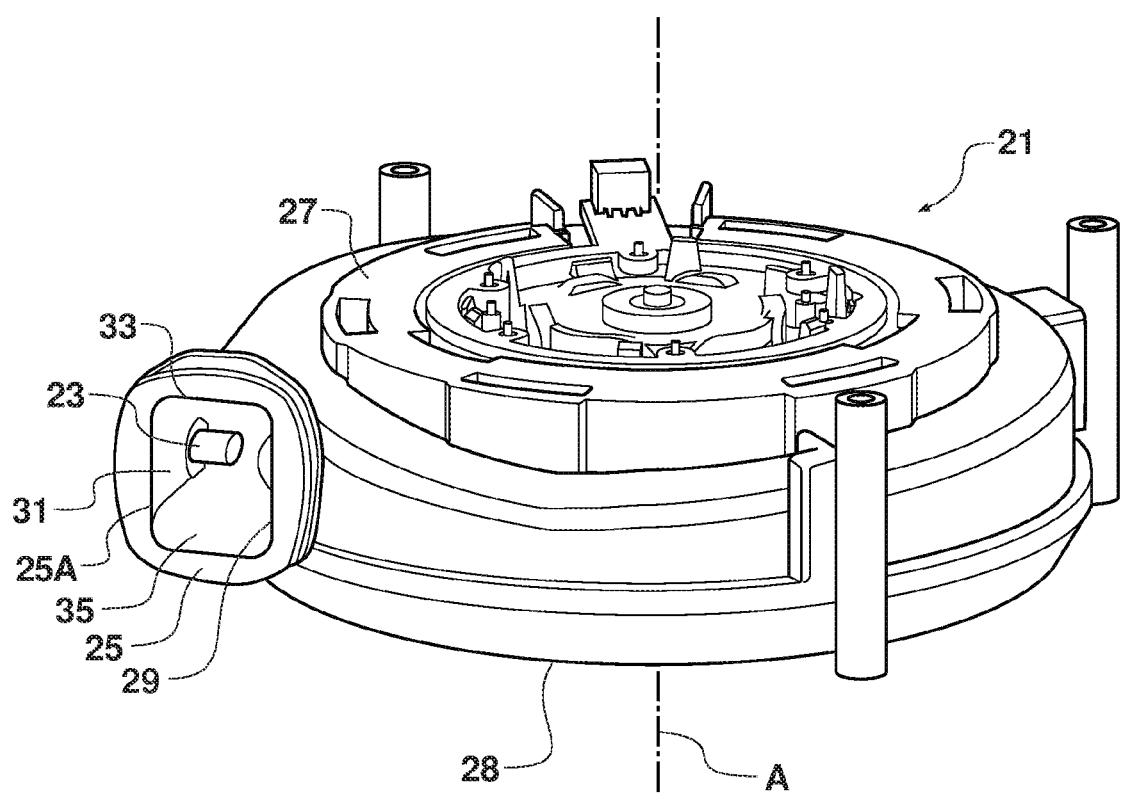
FIG. 2 is a perspective view of a flow generator in accordance with one aspect of the current invention and a sensor of another aspect of the current invention.

With reference to FIG. 2 a respiratory therapy system 1 may comprise, or be configured to be used with, a flow generator to provide a flow of breathable gas to a patient. In this example the flow generator comprises a centrifugal flow generator 21 with a sensor 23 integrated into the flow generator 21. In this example, the sensor 23 is integrated into an outlet 25 of the flow generator 21. The flow generator 21 comprises a generally cylindrical housing 27 comprising an axial inlet 28 extending through a base of the housing 27 and aligned with a longitudinal axis A of the housing 27, the longitudinal axis A being the axis of rotation of an impeller (not shown) of the flow generator 21. The housing 27 further comprises the outlet 25 being a tangential outlet 25 which extends tangentially outwardly of the longitudinal axis A, perpendicularly to that axis A.

The outlet 25 can be said to have an interior surface defined by an inner lateral wall 29, an outer lateral wall 31, an upper wall 33 and a lower wall 35. The inner lateral wall 29 can be defined as the lateral wall closest to the axis A of rotation of the impeller. The outer lateral wall 31 can be defined as the lateral wall radially furthest from the axis A of rotation of the impeller. The interior surface of the outlet 25 comprises the internal surfaces of the aforementioned walls 29, 31, 33, 35 which are adjacent the internal volume of the outlet 25 through which a gas flow is configured to be directed. In the illustrated configuration, the sensor 23 is located on the outer lateral wall 31 of the flow generator 21. The outlet 25 comprises the end of the gas flow path through the flow generator 21 and terminates in an oblong outlet aperture 25A.

In this example, the sensor 23 is incorporated into the flow generator outlet 25. In other examples, the sensor 23 may be located in other locations of the flow path through the flow generator 21, such as in the inlet 28 for example.

Integrated Sensor

Figure 3A:
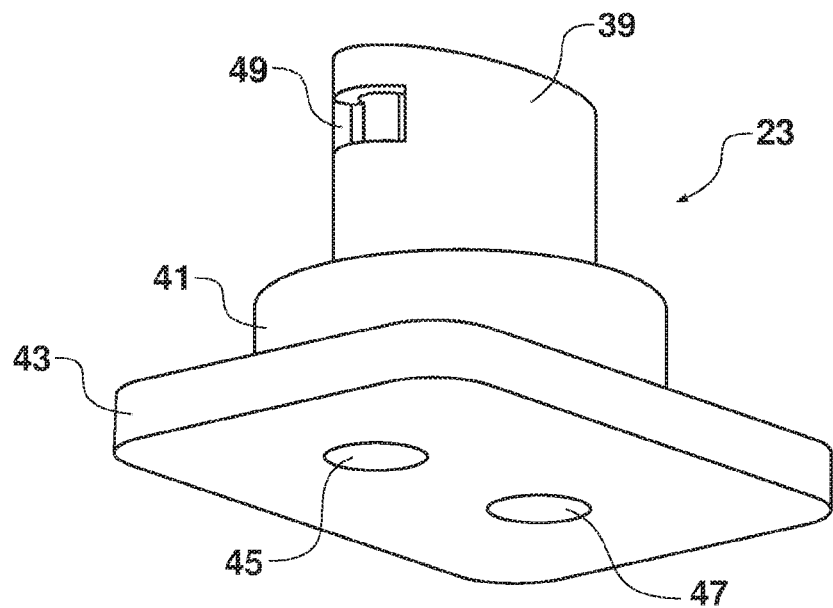
FIGS. 3a and 3b are perspective views of the sensor of FIG. 2.
Figure 3B:
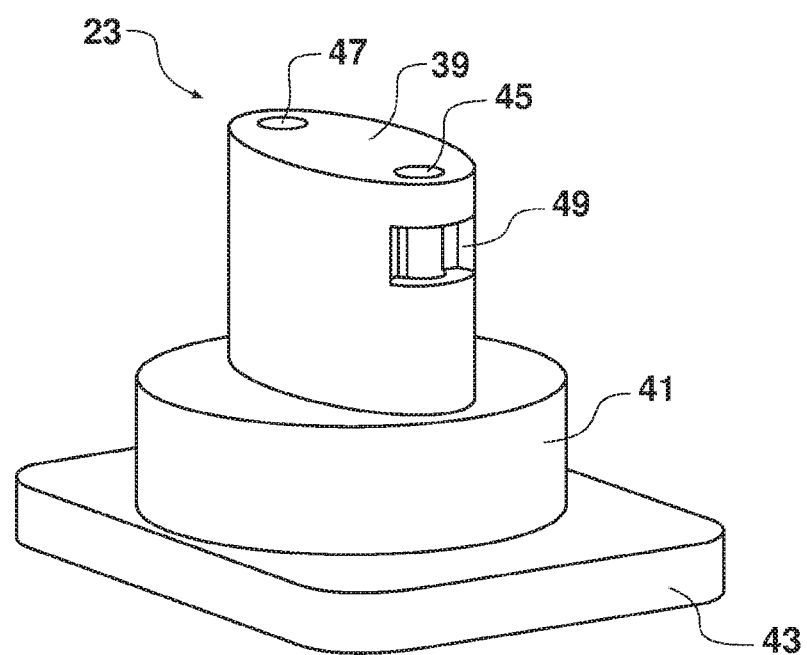
Figure 4:
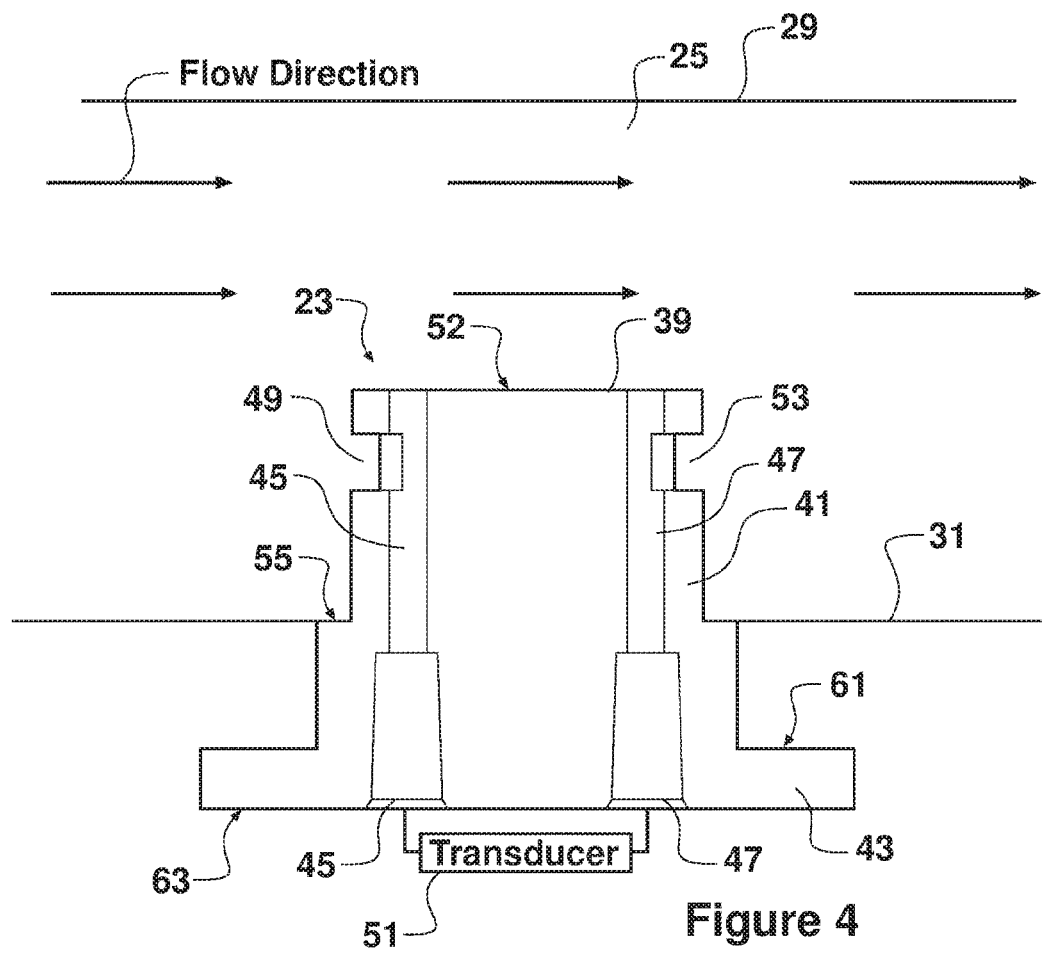
FIG. 4 is a schematic side view of the sensor of FIG. 2 in a gas flow path of the flow generator of FIG. 2.

With reference to FIGS. 3a, 3b and 4 the sensor 23 in this example comprises a differential pressure sensor that can be used as a component in a sensor apparatus. The sensor apparatus includes the sensor 23 and a measuring apparatus, such as a transducer, configured to connect to the sensor 23.

The sensor 23 is adapted to be placed into the gas flow generated by the flow generator 21. In the case of a CPAP machine, the gas flow comprises air. The sensor 23 is coupled to a measuring apparatus which can be an electrical transducer adapted to be responsive to a flow of fluid around or through the sensor 23. The sensor 23 comprises a sensor body including a fluid contacting section 39, an intermediate section 41 and a transducer contacting section 43.

The sensor 23 includes a first internal channel 45 and a second internal channel 47 each spanning the length of the sensor body in a direction that is perpendicular to the gas flow in use. The first internal channel 45 includes a first sensor opening 49, in the flow contacting section 39 of the body 37, configured to face a direction opposite to that of the fluid flow direction. In other words, the first opening 49 faces into the fluid flow. The opposite end of the first internal channel 45 is directed to a first terminal of a transducer 51 which in this example is a differential pressure transducer. The second internal channel 47 includes a second sensor opening 53 configured to face a direction corresponding to that of the fluid flow. In other words, the second opening 53 faces backwards into the wake behind the flow sensor 23. The opposite end of the second internal channel 47 is directed to a second terminal of the transducer 51.

A fluid flowing through a channel can be said to have a static pressure and a dynamic pressure. The static pressure is independent of the fluid's velocity and can be measured by a pressure tap perpendicular to the fluid's flow direction. The dynamic pressure is the kinetic energy per unit volume of a fluid in motion. In other words, a fluid in motion exerts a dynamic pressure on an object in its path. Dynamic pressure is typically measured by a pressure tap pointed directly into the fluid flow stream.

Bernoulli's equation relates a fluid's pressure and velocity and is used to calculate changes in pressure through a system. Bernoulli's equation can be represented as:

$$p + \tfrac{1}{2}\rho u^2 = p\_t \tag{1}$$

Where: p=static pressure; ½ ρu^2=dynamic pressure; p_t=total pressure; ρ=fluid density; u=fluid velocity.

As the first internal channel 45 is directed directly into the fluid (gas) flow stream as shown in FIG. 4, the fluid's total pressure can be measured (the sum of the local random component of the air velocity, and the ordered air velocity). This pressure can be referred to as the total pressure, pitot pressure or stagnation pressure of the fluid. The total pressure is the sum of the static and dynamic pressures of the fluid. As the second internal channel 47 is directed away from the fluid flow stream, the channel is pressurised by the local random component of the fluid velocity, and therefore can be used to indicate the static pressure. In practice, the pressure indicated at the second internal channel 47 is somewhat lower than the undisturbed static pressure.

The pressure transducer 51 can be used to provide an output differential pressure value Δp that assists in determining the flow rate of the gas flow exiting the flow generator 21. The output of the pressure transducer 51 can be referred to as Δp, where:

$$\Delta p = C(\text{total pressure} - \text{static pressure}) \tag{2}$$

Where C is a correction factor, or an appropriate calibration applied to the readings.

The velocity of the fluid can be solved knowing the difference in pressures and the local value for fluid density. From (1):

$$p + \tfrac{1}{2}\rho u^2 = p\_t \rightarrow u^2 = (2(p\_t - p))/\rho = 2\Delta p/\rho \ [m^2/s^2] \tag{3}$$

It should be noted that with low fluid velocity, the differential pressure Δp is relatively small. This increases the difficulty of measuring the value with a transducer. Errors in the measurement can be greater than the measurement itself. This is a reason why the sensor 23 has been placed in a region of relatively high fluid velocity within the flow generator 21.

The small surface area of the flow generator outlet aperture 25a requires the air flow in this region to have a high velocity, and the outlet 25 is therefore an appropriate candidate for a dual pitot probe sensor of the type described in this example.

The velocity can be used to determine the volumetric flow rate of the gas flow through a flat plane of specified surface area by:

$$V = uA \ [m^3/s] \tag{4}$$

Where: V=volumetric flow rate; u=velocity; A=surface area of flow path.

This can then be converted to a flow rate in the desired units. The desired units can be any relevant flow indicating measurement, such as litres per minute (L/min), or cubic meters per minute (m3/min), standard litres per minute, kilograms per second for example.

By providing a double sided sensor 23 comprising two, opposed, sensor openings 49, 53, the sensor 23 may be used in a system 1 where the flow changes direction or reverses, with the functions of the sensor openings 49, 53 reversing accordingly.

Integrated Sensor Location

The centrifugal flow generator 21 includes at least two regions of high fluid velocity, a first at the inlet 28 and a second at the outlet 25. In a first embodiment of the invention, the sensor 23 can be located at the outlet 25. In order to produce accurate, repeatable results, the sensor 23 comprises a probe that is positioned in a suitable high velocity location at the flow generator outlet 25 by projecting into the outlet 25.

The location of the sensor 23 is ideally in a region of the outlet 25 that exhibits consistent fluid flow behaviour among the operating pressure range of the flow generator 21 (for CPAP, 4 cmH2O-20 cmH2O). In other words, the fluid flow should represent the overall flow velocity of the fluid through the system 1 at the location of the sensor 23. Furthermore, the fluid's motion should be similar along a range of flow generator 21 operating parameters (in this case, total pressure or RPM). CPAP devices operate at a pressure known as set pressure. Typically, the set pressure is the pressure of the therapy delivered to a user. In some systems, this set pressure, being a selected characteristic of the breathable gas flow, is typically selected and set by a clinician in advance of use of the system 1, or during titration of the patient using the system 1. The selected set pressure will result in a breathable gas pressure P in the flow path of the system 1. In other systems, the clinician or the system will set a different selected characteristic of the breathable gas flow being a flow rate of breathable gas to be delivered to the patient, and this flow rate will result in a breathable gas pressure P.

This breathable gas pressure P may be measured by one or more pressure sensors at any location within the system 1, and/or may be measured using sensor 23. The breathable gas pressure P is preferably measured in an area of relatively low fluid velocity within the system 1, and may be located, for example, in the flow generator housing 27, in any part of the gas delivery conduit(s) between the flow generator 21 and the patient, and/or in the patient interface itself. In a CPAP configuration, the pressure sensor 20 may be located in the 'end of hose' connector being the tube connector connecting the gas delivery conduit to the patient interface, but is more often located between the blower and the humidifier. It may be desirable to provide a pressure sensor 20 between the flow generator 21 and a humidifier of the system 1. More than one pressure sensor 20 may be provided at different locations within the system 1.

The breathable gas pressure may vary in different parts of the flow path of the system 1. A controller of the system 1 may be configured to process the signal from the or each pressure sensor 20 to account for such pressure variations along the flow path. The system 1 controller may be configured to calibrate the control in accordance with the location of the pressure sensor(s) 20, so that the system 1 achieves the set pressure or flow rate selected. This calibration may, for example, account for a pressure drop between the location of the pressure sensor 20, and the patient. In some circumstances, the breathable gas pressure P may substantially correspond to the delivered gas pressure of the breathable gas flow delivered to the patient. Thus, the breathable gas pressure P may sometimes correspond to the set pressure which the system 1 is aiming to deliver to the patient, depending on where along the gas flow path the breathable gas pressure is measured.

The breathable gas pressure may be measured using the downstream opening 53 of sensor 23, downstream opening 53 being located in an area of relatively low gas velocity within the system 1. In another example, the breathable gas pressure may be measured via a further opening or flow channel which is in communication with downstream opening 53, for example via downstream flow channel 47 of sensor 23. The further flow channel may be branched off the downstream flow channel 47. In other examples, the breathable gas pressure may be measured using an opening into the breathable gas flow located in another part of the system 1, such as in the wall of the outlet 25 of the flow generator 21, or through a wall of another part of the system 1.

Figure 5A:
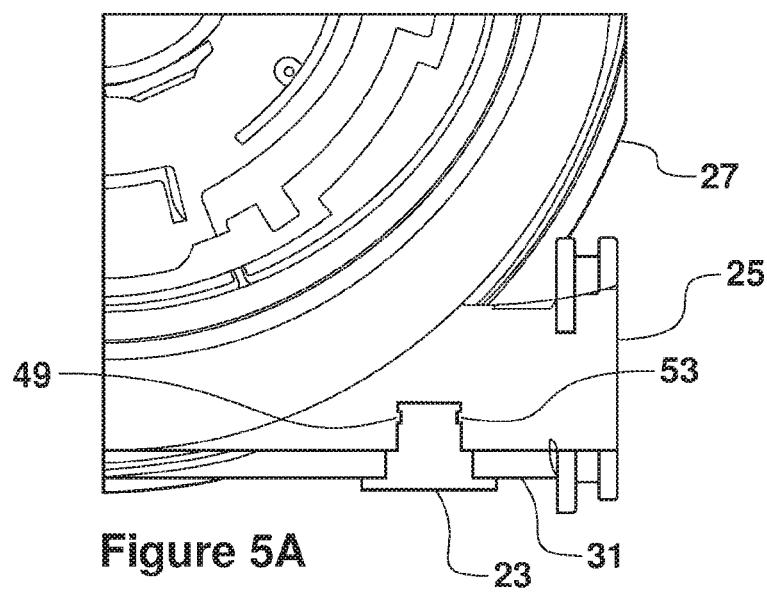
FIGS. 5a and 5b are enlarged sectional plan views of part of the flow generator of FIG. 2

The first sensor opening 49 of the first internal channel 45 receiving incoming fluid from the gas flow path through the outlet 25 is configured to receive flow representing the overall velocity of the fluid flow through the system 1. FIG. 5A shows a cross sectional view of an embodiment of the centrifugal flow generator outlet 25 configured to include a sensor 23. In the illustrated configuration, the probe, or flow contacting section 39 of the sensor 23 is configured to be on the radially outermost lateral wall 31 of the outlet 25.

The sensor 23 projects from the outer lateral wall 31 of the outlet 25 into the internal volume of the outlet 25. The first opening 49 is spaced apart from the interior wall 29 of the generator outlet 25 so as to mitigate the influence of boundary layer effects between the fluid and the interior surface. The channel 45 provides a total pressure reading to the first terminal of the transducer 51.

The second opening 53 is configured to face approximately the opposite direction to the first opening 49 of the first internal channel 45. The second internal channel 47 provides a reading slightly below the static pressure of the fluid to the second terminal of the transducer 51.

The transducer 51 uses the total pressure reading and the approximate static pressure reading to determine an electrical output $\Delta p$. $\Delta p$ can then be used to determine the velocity of fluid flow from equation (3), and therefore the volumetric flow of the gas flow in the flow generator 21, from equation (4).

Figure 5B:
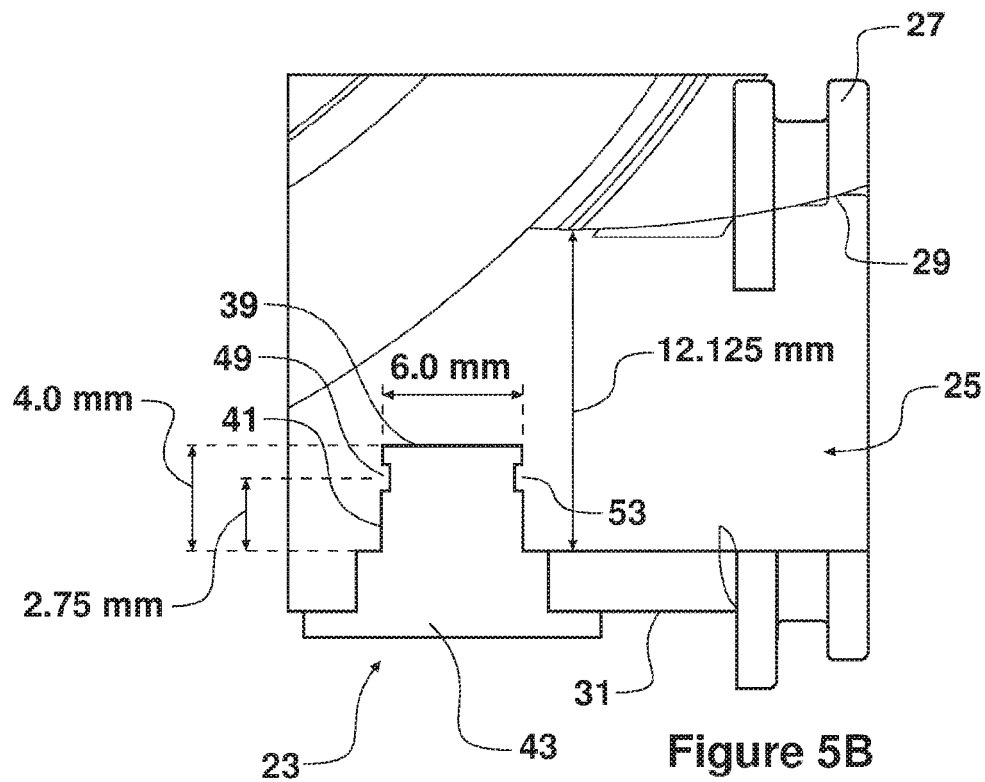
Figure 14:
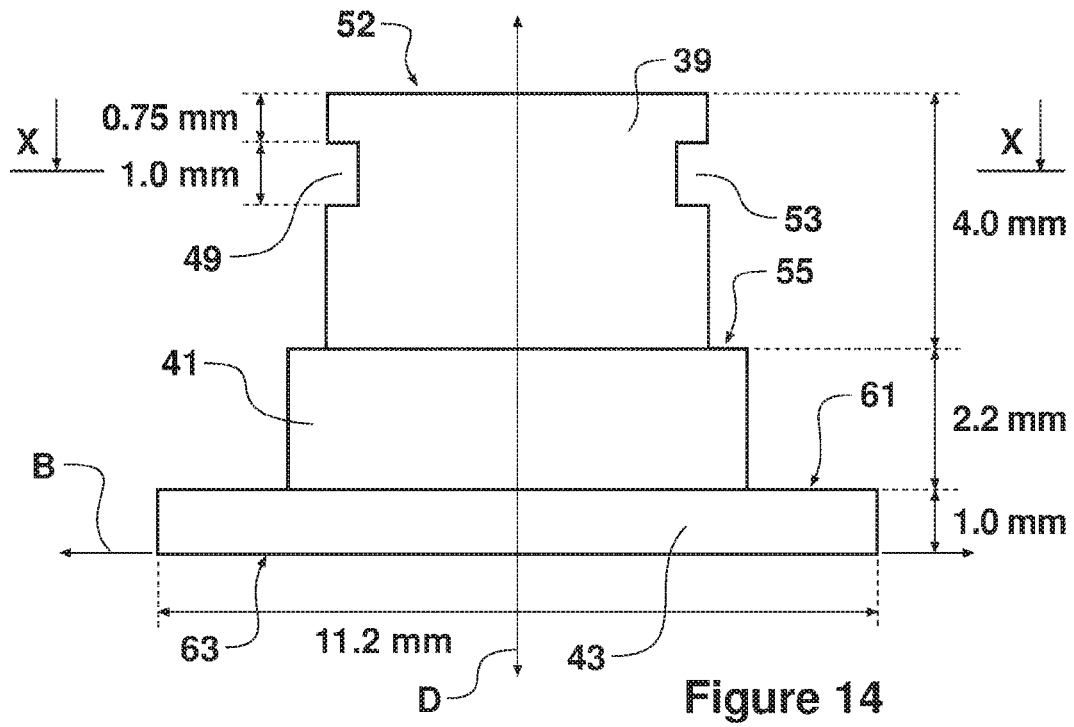
FIG. 14 is a side view of the sensor of FIG. 2.

With particular reference to FIGS. 5B and 14, the probe or fluid contacting section 39 is configured to extend a total distance, in this example, of approximately 4.0 mm from the internal surface of the outer lateral wall 31 of the outlet 25. The inner and outer lateral walls 29, 31 of the outlet 25 in this example are spaced apart by about 12.1 mm. In some examples, the fluid contacting section 39 projects less than half way across the outlet 25, between the inner and outer lateral walls 29, 31, and in this example projects about a third of the distance across the outlet 21. In this example, the first opening 49 and second opening 53 of the flow sensor 23 are configured such that their central points are displaced approximately 2.75 mm from the internal surface of the outer lateral wall 31. This distance can be important. If the displacement of the central points of the first opening 49 and second opening 53 from the internal surface of the outer lateral wall 31 is too small, boundary layer effects influence the readings in a detrimental way, and if this distance is too large, there are turbulent effects of the opposing internal surface of the inner lateral wall 29 of the flow generator outlet 25, that affect the readings in a detrimental way.

The distance between the internal surface of the inner lateral wall 29 and the internal surface of the outer lateral wall 31 is approximately 12.1 mm. In other words, 12.1 mm is the lateral dimension of the outlet 25 at the location of the probe or fluid contacting section 39. In this example, the ratio between the probe and the outlet 25 lateral dimension is approximately 4.0:12.1, or 1:3.025. This ratio was found to be sufficient to provide repeatable readings for $\Delta p$ whilst minimising the effect of the flow sensor 23 on the fluid flow through the outlet and downstream components. The ratio of the distance from the outer lateral wall 31 of the outlet 25 to the sensor openings 49, 53 and the distance between the internal surface of the inner lateral wall 29 and the internal surface of the outer lateral wall 31 is important for accurately measuring flow. In the current example this ratio is 2.75:12.1, or 1:4.4.

Figure 6:
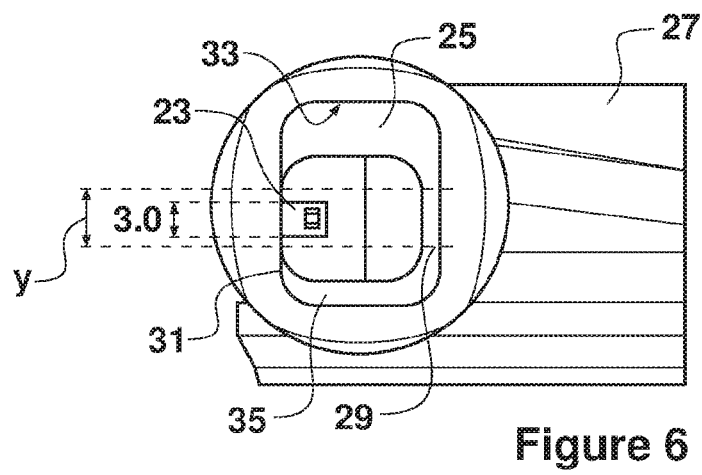
FIG. 6 is a view, in the direction of the gas flow path, of an outlet of the flow generator of FIG. 2 in which the sensor is mounted.
Figure 13:
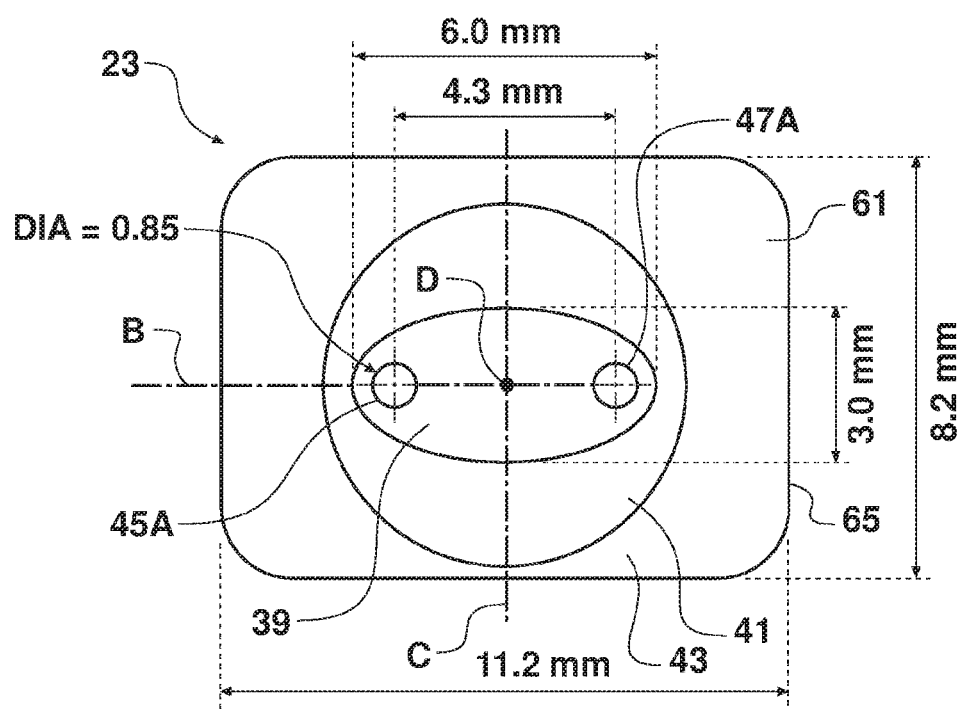
FIG. 13 is a plan view of the sensor of FIG. 2.

With reference to FIG. 6 the fluid contacting section 39 of the sensor 23 projects from the outer lateral wall 31 of the outlet 25 into the internal volume of the outlet 25. The probe or fluid contacting section 39 is approximately centrally located with reference to a vertical dimension of the outlet 25, that is, with reference to the distance between the upper and lower walls 33, 35 of the outlet 25. In this example, and with reference to FIGS. 6 and 13, the height or vertical dimension of the probe or fluid contacting section 39, when in use and viewed along the axis of outlet 25, is approximately 3.0 mm. In the illustrated configuration, the vertical dimension of the internal volume of the outlet 25 increases along the fluid flow path from the volute to the end of the generator outlet 25, that is when the outlet 25 is viewed from the side and perpendicular to the direction of gas flow. The probe 39 can be said to be positioned centrally with respect to the volute outlet 25. In at least one embodiment, the probe 39 can be positioned within the central third Y of the volute outlet 25 as considered in a direction parallel with the axis of rotation A, as shown in FIG. 6.

In other examples, the probe 39 can be located on any of the upper, lower or inner lateral walls of the flow generator outlet 25.

Gas Flow Control

Figure 7:
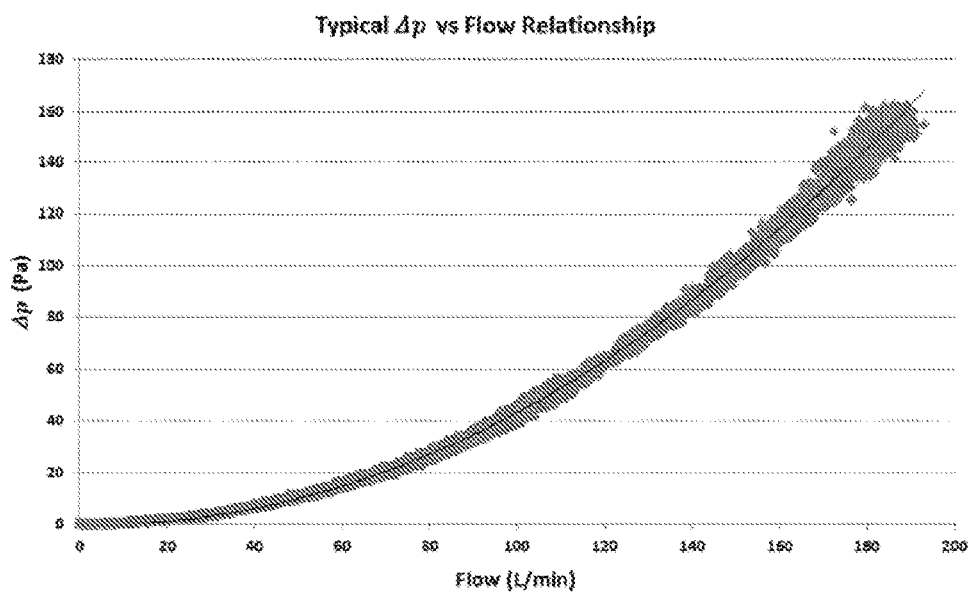
FIGS. 7 to 12 are graphs showing the relationship between different variables of the gas flow that can be used by a controller of the flow generator of FIG. 2 to control the gas flow.

Under ideal flow conditions, a measured value of $\Delta p$ will produce a corresponding volumetric flow rate V independent of the operating range of selected set pressures of the flow generator 21. In other words, there is a very close or identical correspondence between values of $\Delta p$ and values of V across the operating range of set pressures of the flow generator 21. FIG. 7 shows a typical relationship between $\Delta p$ and V for a laminar fluid flow.

Under real conditions within the flow generator outlet 25, the probe 39 does not encounter perfectly laminar flow. This is due to a variety of factors, including surface effects of the interior surface of the flow generator outlet 25 and the increasing cross sectional area of the flow generator outlet 25 as the gas flow passes from the volute of the flow generator 21 to the end aperture of the outlet 25. The presence of the sensor 23 itself impacts the flow to an extent. The above and below factors contribute to non-laminar flow which means that the fluid flow through the outlet 25 of the flow generator 21 differs to an extent as the breathable gas pressure of the system 1 is increased. This is at least partially as a result of turbulence induced by the close proximity of the impellor blades within the flow generator housing 27.

Figure 8:
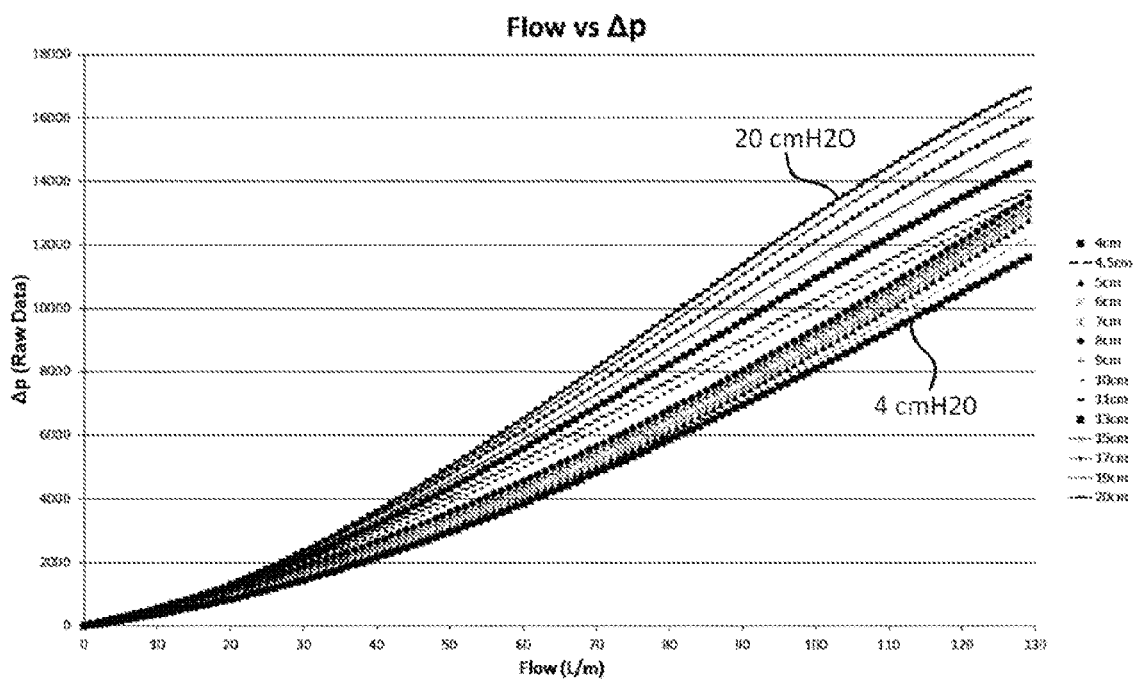

FIG. 8 shows the relationships between Δp and V determined from a sensor 23 placed on the outer lateral wall 31 of the outlet 25 of flow generator 21 for breathable gas pressures ranging from 4 cmH2O-20 cmH2O. For this data, the probe 39 was configured as shown in FIG. 6.

The results indicate that a different reading for differential pressure Δp is produced for each breathable gas pressure P of the system. In other words, when the system is operating at a breathable gas pressure P of 4 cmH2O, the reading of Δp is different for a given flow rate than a reading of Δp when the system is operating at a breathable gas pressure P of 20 cmH2O.

System Controller Operation

The flow generator 21, and in particular the rotational speed and/or torque of the impeller, is controlled by one or more electronic controllers, such as one or more microprocessors, which comprise part of the flow generator 21, or comprise part of the larger system 1 but are in communication with the flow generator 21. One or more controllers may be provided as required. The or each controller may be configured to communicate with one or more controllers that are external of the system 1, such as a separate controller, or a remote server for example.

The controller controls the rotational speed and/or torque of the impeller to deliver the characteristics of the breathable gas flow that are selected, either by a clinician or by the controller itself. Thus if a set pressure of 4 cmH2O is selected, the controller controls the rotational speed and/or torque of the impeller to deliver a gas flow to the patient at a breathable gas pressure that corresponds to the set pressure.

However, the location of the sensor 23 in the flow generator 21 itself, and in particular in the inlet 23 or outlet 25 of the housing 27 of the flow generator 21 makes it difficult for the controller to determine the control signal required to control the flow generator impeller because of the variation described above of the relationship between differential pressure Δp and volumetric flow rate V for different breathable gas pressures P.

As will be described in more detail below, data can be obtained, as per the graphs of FIGS. 8 and 9, which indicates how differential pressure Δp varies in relation to the volumetric flow rate V, for a range of different, discrete breathable gas pressures P. Such data can be obtained by testing. However, it can be difficult to subsequently determine a volumetric flow rate V that results from a breathable gas pressure P that differs from the particular discrete breathable gas pressures that have been tested. It is important to be able to accurately do this, to ensure that the system 1 can accurately operate to provide any particular breathable gas pressure P that might be selected or required. In other words, the flow rate V is being used by the controller to generate a control signal used to determine the speed and/or torque of the impeller motor.

The controller of the system 1 include processing steps that are configured to calculate, or predict or estimate or look-up the volumetric flow rate V that will result from any given set pressure P within a realist range. In one example any set pressure between about 4 and 20 cmH2O. For a bi-level system, the set pressure may be in the range of about 0 and 40 cmH2O.

The controller of the system 1 is configured to control the rotational speed and/or torque of the impeller to provide the breathable gas flow with a selected characteristic, wherein the selected characteristic results in a corresponding breathable gas pressure of the breathable gas being delivered to the patient. The selected characteristic may be a pressure (set pressure), or may be a flow rate (set flow-rate), and this may be manually set by a clinician, or automatically set by the system 1. For example it may be desirable in a CPAP type system to deliver a breathable gas at a selected set pressure. In other types of therapy it may be desirable to deliver a breathable gas at a selected set flow rate.

The controller of the system 1 is operative according to:
a) a first process step wherein the output from the integrated sensor 23 is used to generate a signal indicative of differential pressure between the first and second sensor openings in the gas flow path, and
b) a subsequent process step wherein the signal indicative of differential pressure is used by the controller to generate a flow rate signal indicative of the flow rate of the breathable gas flow.

The flow rate signal of the subsequent process step is generated in dependence upon a pre-determined indication of the variance of the relationship between differential pressure and flow rate of the breathable gas flow at a plurality of discrete, different, breathable gas pressures, such that the flow rate signal that is generated varies in dependence upon the breathable gas pressure which corresponds to the selected characteristic of the breathable gas flow. In other words, whether the system 1 is controlling to deliver a set pressure or a set flow rate to the patient, the controller is matching the set pressure or set flow rate to the breathable gas pressure that would result at the patient, and then calculating flow rate from the measured differential pressure and accounting for the non-linear relationship between differential pressure and flow rate that occurs for different breathable gas pressures. Where the selected characteristic is set pressure, the breathable gas flow is the variable, and where the selected characteristic is set flow, the breathable gas pressure is the variable. The controller can then adjust the motor speed and/or torque accordingly.

The controller is configured to compare the breathable gas pressure corresponding to the selected characteristic with the plurality of discrete, different, breathable gas pressures for which there is the pre-determined indication of the variance of the relationship between differential pressure and flow rate of the breathable gas flow, to match the corresponding breathable gas pressure with one of the plurality of discrete, breathable gas pressures, and to subsequently generate the flow rate signal with reference to the predetermined relationship between differential pressure and flow rate for the matched breathable gas pressure.

The controller is further configured if as a result of the comparison, the breathable gas pressure does not correspond to one of the plurality of discrete, breathable gas pressures, to generate the flow rate signal in dependence upon a signal indicative of an interpolation between the known predetermined relationship between differential pressure and flow rate for discrete breathable gas pressures above and below the selected breathable gas pressure.

The signal indicative of the interpolation may be generated as a result of a calculation by the controller, the calculation being any one or more of:

a) a line of best fit;
b) a logarithmic function;
c) an exponential function;
d) a polynomial function.

The signal indicative of the interpolation may be generated as a result of a calculation by the controller referencing a look-up table.

In one example, a line of best fit of order 3 (3rd order polynomial) is fit to each of the data sets shown in FIG. 8 using a least squares regression method, where differential pressure $\Delta p$ is the independent variable and flow rate V is the dependent variable. In at least one embodiment, a line of best fit of order 4, 5 or 6 can be used. In at least one embodiment, an estimation using a logarithmic function can be used. In at least one embodiment, an estimation using an exponential function can be used.

An equation of order 3 with respect to $\Delta p$ is used for the function V($\Delta p$) as it provides a coefficient of determination closest to 1 when compared with other linear regression fits (i.e. of order 2 or 4 etc.). The coefficient of determination is a number that indicates the proportion of the variance in the dependent variable that is predicted from the independent variable. It provides a measure of the effectiveness of how a model replicates observed outcomes. Equations of order 1 and 2 have coefficients of determination further from 1 than the equation of order 3 in the illustrated configuration.

The line of best fit is then used to determine the values of V from corresponding $\Delta p$ values that don't correspond with one of the discrete measurement points shown. Measurements of V, $\Delta p$ and P have been determined for breathable gas pressures of 4, 4.5, 5, 6, 7, 8, 9, 10, 11, 13, 15, 17, 19 and 20 cmH2O. The lines of best fit allow accurate estimation of $\Delta p$ and V over the spectrum of breathable gas pressures for which measurements have been taken.

The skewed results of FIG. 8 (where $\Delta p$ is greater for a fixed V when comparing different breathable gas pressures P) are likely due to the turbulent flow characteristics of the fluid in the outlet 25 of the flow generator 21 at various breathable gas pressures. The air flowing through the outlet 25 behaves differently (with relation to the interior volume of the outlet) at higher breathable gas pressures than at lower breathable gas pressures. As a result, the flow is not of identical characteristics across the various breathable gas pressures of the system 1. In a situation where the flow is not known (i.e. under normal operating conditions), the differences in the curves at various flow rates can be accounted for through calibration to provide an accurate estimate of the flow.

Figure 9:
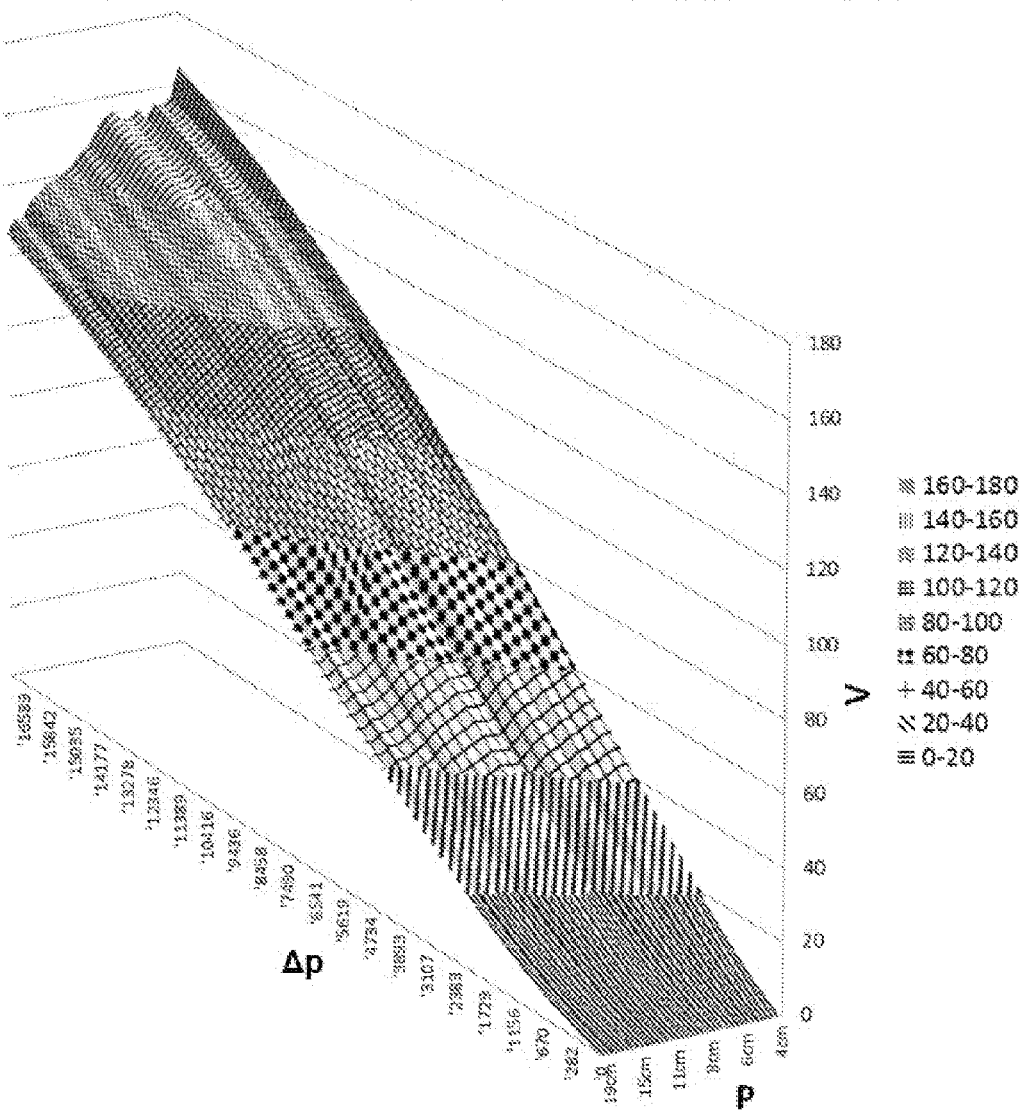

FIG. 9 shows a second way of representing the relationship between $\Delta p$ and V on a graph with three axes. Generating a smooth approximation of the surface shown in FIG. 9 can allow a determination of V across the entire operating range of breathable gas pressures of the flow generator 21. Under normal operation. $\Delta p$ and P are both measured variables while flow V is an unknown variable. The flow V is however clearly dependent on both $\Delta p$ and P, and can therefore be represented:

$$V = f(\Delta p, P)$$

In other words, flow V is a function of $\Delta p$ and P.

As it is not possible for empirical measurements of V, $\Delta p$ and P to be made for every incremental breathable gas pressure of the system 1, a means of estimating the flow rates of intermediate set pressures (i.e. 6.3 cmH2O) based on a fixed spectrum of empirical measurements was devised. For the intermediate breathable gas pressures, the relationship between V, $\Delta p$ and P is estimated such that with measured values of $\Delta p$ and P, one can determine a satisfactory estimate of V.

What constitutes a satisfactory estimate of V varies depending on the particular application in which the above flow generator 21 with an integrated sensor 23 is used. Different respiratory therapy systems 1 may require different flow sensor accuracy requirements, and/or have different physical layouts which affect the sensor output. In some applications, this may be defined by V±5%, in other applications, it may be defined by V±10%.

The breathable gas pressure of an earlier prior art respiratory therapy system of Fisher & Paykel Healthcare Limited, marketed under the name ICON, is capable of being adjusted in increments of 0.2 cmH2O and the set pressure of other systems may be capable of being adjusted in increments of 0.1 cmH2O. A data resolution of at least 0.1 cmH2O is therefore desirable in some example systems.

In order to do this, one can form a surface of best fit across the known data points (similar to that shown in FIG. 9, although the surface of FIG. 9 is not a surface of best fit based on linear regression). As every point on the surface can be calculated, V can always be estimated from measured $\Delta p$ and P values.

Each of the curves shown in FIG. 8 are approximated by a function of the order $\Delta p\hat{\,}3$. As the total breathable gas pressure P is also an independent variable, it is known that the relationship between V, $\Delta p$ and P can be of the form:

$$V = [A(P)]\Delta p\hat{\,}3 + [B(P)]\Delta p\hat{\,}2 + [C(P)]\Delta p + \text{Constant}$$

Where A(P), B(P) and C(P) are functions where P is the independent variable. The constant is known to be 0 as the flow rate is 0 when the set pressure is 0. So:

$$V = [A(P)]\Delta p\hat{\,}3 + [B(P)]\Delta p\hat{\,}2 + [C(P)]\Delta p$$

Functions for A(P), B(P) and C(P) are determined using the known dataset that is shown in FIGS. 8 and 9.

In order to generate FIGS. 8 and 9, an equation of order 3 was determined such that it was a line of best fit to represent the data for each breathable gas pressure. The equations determined allow the coefficients A(P), B(P) and C(P) to be approximated numerically. For example, at a set pressure of 4 cmH2O, the constants A(P), B(P) and C(P) can be approximated from the linear regression line of best fit of order 3 with $\Delta p$ as the independent variable. This can be done for every breathable gas pressure for which a complete data set is acquired.

This process can be completed for each of the breathable gas pressures for which measurements were taken, generating various expressions for the cubic line of best fit for V in terms of $\Delta p$ at each discrete breathable gas pressure P. The values of functions A(P), B(P) and C(P) are extracted from these expressions.

Figure 10:
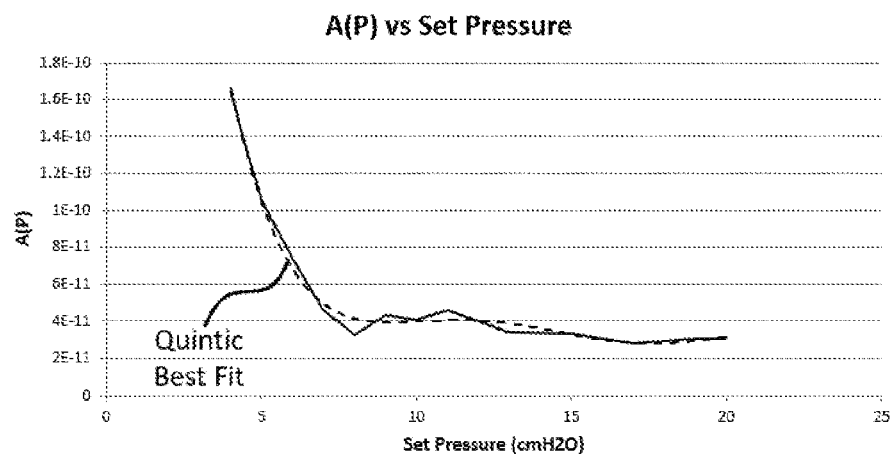

An estimate of the function A(P) over the range of breathable gas pressures is then determined using the discrete values for A(P). The measured values for A(P) are plotted such that breathable gas pressure is the independent variable and A(P) is the dependent variable. The plot for the illustrated configuration is shown in FIG. 10. A line of best fit is generated (again by linear regression). For the function A(P), the function that models the measured data to a high enough degree of accuracy (i.e. coefficient of determination closest to 1) is determined to be of order 6. In alternate applications of the invention, the function can be a polynomial of different order, for instance of order 1-5 or 7-8 or higher. Alternatively, the function can be a logarithmic function, an exponential function, or any other function that approximates the data set of the given application. The polynomial in this case is again determined by comparing the coefficient of determination for lines of best fit derived from linear regression of orders 1-6.

Similar methodology is applied to functions B(P) and C(P), allowing an approximation of each function. The function that models the measured data for B(P) is determined to be of order 5. The function that models the measured data for C(P) is determined to be of order 3.

Figure 11:
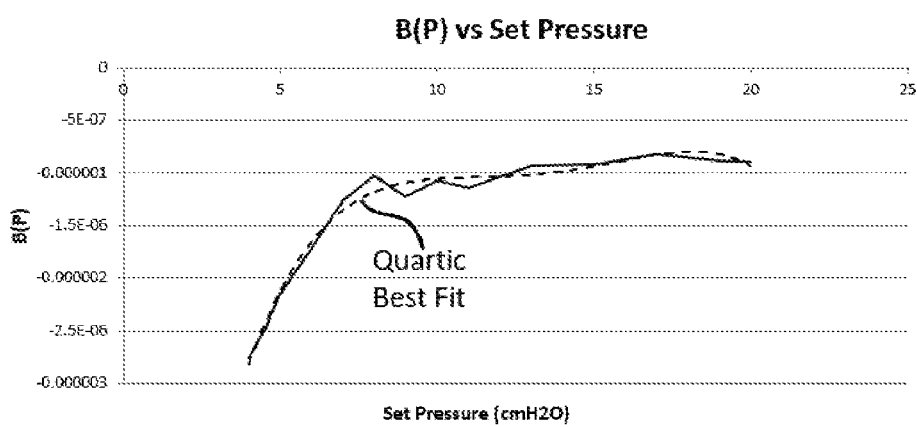
Figure 12:
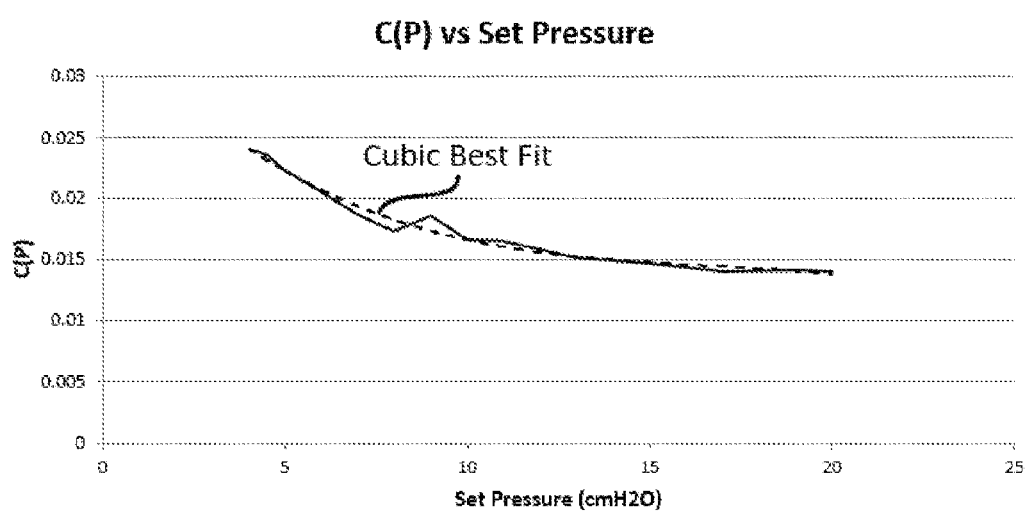

FIGS. 10 to 12 respectively show a representation of the functions A(P), B(P), C(P) across the operating range of breathable gas pressures of the system 1.

These functions are valid across the entire operating range of the system 1. As a result, V can be estimated using measured values of $\Delta p$ and P using:

$$V=[A(P)]\Delta p\char`\^3+[B(P)]\Delta p\char`\^2+[C(P)]\Delta p$$

At a specified breathable gas pressure, the correct values for A(P), B(P) and C(P) are determined using the relationships shown in FIGS. 10, 11 and 12. The measured value for $\Delta p$ is then introduced, allowing V to be determined. The model derived allows the flow rate to be estimated across the entire range of breathable gas pressures the system 1 may be configured to deliver without the need to have an independent data set corresponding to each variation of conditions.

Lookup Table with Linear Interpolation

The above method of determining the flow rate from the measured data disclosed previously involves using a number of reasonably complex functions and a known data set determined empirically to determine the flow rate V. This level of computation can require a substantial amount of computational power. A second application of the above method can use lookup tables of a defined resolution, and linear interpolation if values of a higher resolution are required to provide the required data of the functions A(P), B(P) and C(P), and accordingly reduce the computational power required by the host device substantially.

First Lookup Table Method

A first method of implementing a lookup table to simplify the computations of the system 1 involves storing a table of empirically determined values for $\Delta p$, A(P), B(P) and C(P) for a range of breathable gas pressures. For instance, a table can be stored for a breathable gas pressure of 4.0 cmH2O resembling:

| P = 4.0 cmH$_2$O | | | |
|---|---|---|---|
| $\Delta p$ | A(P) | B(P) | C(P) |
| 0 | $A_{\Delta p-0}$ | $B_{\Delta p-0}$ | $C_{\Delta p-0}$ |
| 1 | $A_{\Delta p-1}$ | $B_{\Delta p-1}$ | $C_{\Delta p-1}$ |
| 2 | $A_{\Delta p-2}$ | $B_{\Delta p-2}$ | $C_{\Delta p-2}$ |
| x | $A_{\Delta p-x}$ | $B_{\Delta p-x}$ | $C_{\Delta p-x}$ |

The values for A_($\Delta p$=x), B_($\Delta p$=x) and C_($\Delta p$=x) are all calculated via the formulae disclosed above and pre-loaded into the table for P=4.0 cmH2O and $\Delta p$=x (where x spans the range of all measured values of $\Delta p$ at P=4.0 cmH2O at a pre-determined resolution). With this table pre-loaded onto the system 1, when the system 1 operates at a breathable gas pressure of P=4.0 cmH2O, a reading can be determined for $\Delta p$ from the flow sensor 23, and the system 1 can then reference the look up table to determine A(P), B(P) and C(P), as opposed to calculating them using the formulae previously disclosed. The flow rate can then be calculated using:

$$V=[A(P)]\Delta p\char`\^3+[B(P)]\Delta p\char`\^2+[C(P)]\Delta p.$$

The use of a lookup table as opposed to the polynomial equations for (P), B(P) and C(P) reduces the computational requirements of the system on which the calculations are being made.

Similar pre-loaded look up tables can be stored on the machine for P=5.0 cmH2O, P=6.0 cmH2O etc. For an interval of pressure of 0.5 cmH2O, in one embodiment, a lookup table for each interval of breathable gas pressure can be stored in the system 1.

Second Lookup Table Method

A second method of implementing a lookup table to simplify the on-board computations of the system 1 involves storing a table of empirically determined values for P and the corresponding values of A(P), B(P) and C(P) according to the previously disclosed formulae.

For instance, a table can be stored resembling:

| P (mmH$_2$O) | A(P) | B(P) | C(P) |
|---|---|---|---|
| 4.0 | $A_{p-4.0}$ | $B_{p-4.0}$ | $C_{p-4.0}$ |
| 5.0 | $A_{p-5.0}$ | $B_{p-5.0}$ | $C_{p-5.0}$ |
| 6.0 | $A_{p-6.0}$ | $B_{p-6.0}$ | $C_{p-6.0}$ |
| x | $A_{p=x}$ | $B_{p=x}$ | $C_{p=x}$ |

The values of A_(P=x), B_(P=x) and C_(P=x) for each discrete P value can be determined from the formulae and pre-loaded into the table. When the system is then operating at a known breathable gas pressure, say P=4.0 cmH2O, the values of A_(P=4.0), B_(P=4.0) and C_(P=4.0) can be taken from the lookup table, the value of $\Delta p$ can be read from the flow sensor 23, and the values can be used to determine V according to:

$$V=[A(P)]\Delta p\char`\^3+[B(P)]\Delta p\char`\^2+[C(P)]\Delta p$$

In a first embodiment, the lookup table can store values for A_(P=x), B_(P=x) and C_(P=x) with x at intervals of 0.1, corresponding to the highest resolution of breathable gas pressure the system can operate at (in other applications, this resolution may be different, and the table can include higher or lower resolutions as required).

In a second embodiment, the lookup table can store values for A_(P=x), B_(P=x) and C_(P=x) with x at intervals that are greater than the smallest breathable gas pressure resolution of the machine, for instance x=0.5. In this case, linear interpolation can be used to determine an intermediate value for each of A_(P=x), B_(P=x) and C_(P=x). For example, if the lookup table includes values for P=4.0 and P=4.5, but the system is operating at P=4.2, the constants for A_(P=4.2), B_(P=4.2) and C_(P=4.2) can be determined in the following way:

Look up A_(P=4.0) and A_(P=4.5) from the lookup table.

$$A\_(P=4.2)=A\_(P=4.0)+[((A\_(P=4.5)-A\_(P=4.0)))/5\times 2]$$

The value for A_(P=4.2) is determined by linear interpolation of the two surrounding known values, A_(P=4.0) and A_(P=4.5). The same method can be used to linearly interpolate values for B_(P=4.2) and C_(P=4.2), which can then be used to determine V. Using linear interpolation in such a way has an advantage of reducing the storage requirements of the lookup table, as values for A(P), B(P) and C(P) are required to be stored for a lower number of P values, however the linear interpolation will not model the functions for A(P), B(P) and C(P) perfectly, and as such, an error is introduced into the calculation.

Sensor Design

The sensor 23, described above with reference to FIGS. 2, 3 and 4 is designed in such a way as to provide a differential pressure reading Δp that can be used to determine the flow rate V, whilst minimising the loss of kinetic energy of the gas flow through the flow generator outlet 25 as the flow passes the probe 39.

The probe or fluid contacting section 39 of the sensor 23 is configured to be in contact with the fluid passing through the outlet 25 of the flow generator 21. The intermediate section 41 is configured to be sealed to the housing 27 of the flow generator 21. The intermediate section 41 is sealed to the housing 27 of the flow generator 21 to prevent fluid from permeating through the join between the intermediate section 41 and the housing 27. The thickness of the intermediate section 41 may be arranged to substantially correspond to the thickness of the outer lateral wall of the outlet 25. The transducer contacting section 43 is configured to be connected to the transducer 51 or sensor providing a differential pressure reading, external of the outlet 25 and the gas flow path.

With reference to FIGS. 13 to 18, the sensor 23 includes a longitudinal axis B, a lateral axis C and a vertical axis D. A horizontal plane can be defined as the plane formed by the longitudinal axis B and the lateral axis C. In this example, the sensor 23 is symmetrical about the lateral axis C. In other examples, the sensor 23 may be assymetric.

The intermediate section 41 projects vertically from the first transducer contacting section 43. The fluid contacting section 39 projects vertically from the intermediate section 41. The fluid contacting section 39 is oval shaped when viewed in plan, that is, when viewed along vertical axis D. An oval/elliptical shape has been determined to provide the most consistent results. The longer dimension of the oval fluid contacting section 39 when viewed in plan is approximately 6.0 mm in this example. The shorter dimension of the oval fluid contacting section 39 when viewed in plan is approximately 3.0 mm in this example, but in other examples could be in the range of 2-4 mm. In other words, the ratio between the longer and shorter dimensions of the oval fluid contacting section is approximately 2:1 in this example, but in other examples could be in the range of 3:2 to 3:1. This ratio, or a ratio similar to this was found to provide the most accurate results for Δp. The reasoning for this relates to the range of the differential pressure sensor/transducer 51. A particular differential pressure transducer used in this example is the Sensirion SDP3x. The transducer has a differential pressure range of ±500 pa. The configuration of the flow sensor 23 with a major to minor axis ratio of about 2:1 was found to maximize the use of the flow sensor's pressure range, decreasing associated measurement errors.

The following characteristics of the shape of the fluid contacting portion 39 can be used to achieve the desired accuracy and reliability of data measurement of the sensor 23:

a) the thickness of the fluid contacting section 39, that is, the shorter dimension of the oval fluid contacting section 39 when viewed in plan, along axis D;

b) the ratio of length to width when viewed in plan, along axis D;

c) the curvature of one or more quadrants of the fluid contacting portion 39, when viewed in plan, along axis D;

d) the radius of curvature of the flow facing parts of the fluid contacting portion 39.

Other embodiments can use any other relevant differential pressure transducer for the same effect.

To illustrate this, in one example a sensor is capable of providing a reading for Δp on a scale of 0 (minimum range value) to 100 (maximum range value), with an error of ±2. If the design of the flow sensor 23 for a given set of flow conditions typically provides sensor readings in a range of 60-80, the error of ±2 represents approximately 2.5-3.3% error. If the design of the flow sensor 23 is altered such that, for the same given set of flow conditions, the flow sensor 23 provides readings in the range of 10-15, the error of ±2 represents approximately 13.3-20% error, substantially more than the 2.5-3.3% error of the initial design. The readings produced by the sensor 23 with the first example are therefore more desirable as the error is less. It was found that, for the Sensirion SDP3x transducer, the major to minor axis ratio of 2:1 produced readings that represented a substantial portion of the sensitivity of the flow sensor 23. This design parameter is therefore important in the provided flow generator 21, and sensor 23 configuration to produce accurate results.

The fluid contacting section 39 terminates in a fluid contacting section horizontal, planar surface 52. The fluid contacting section horizontal surface 52; and the vertical profile of the fluid contacting section is oval/elliptical when viewed in plan to enhance its aerodynamic characteristics when in a fluid flow. The shorter length of the oval along axis C is aligned such that it is approximately perpendicular to the direction of fluid flow. Accordingly, the longer length of the oval along axis B is aligned such that it is approximately parallel to the direction of fluid flow. As a result, fluid is able to divert with minimal perturbation around the fluid contacting section 39 whilst still enabling the probe 39 to measure the required pressure readings. In alternate configurations, the fluid contacting section or probe 39 may have a profile when viewed from the top resembling that of a diamond, circle, rectangle or another profile.

The intermediate section 41 terminates in an intermediate section horizontal surface 55. In the illustrated embodiment, the intermediate section horizontal surface 55 has a circular profile when viewed in plan. The purpose of the intermediate section 41 is to act as a contact region, and a region of support, between the sensor 23 and the housing 27 of the flow generator 21. Furthermore, the intermediate section 41 of the sensor 23 acts as a portion of a seal between the internal volume of the flow generator outlet 25 and the external volume. The shape of the intermediate section 41 is therefore not particularly limited, so long as it is capable of providing accurate support for the sensor 23 in the fluid flow and a seal can be formed between the internal volume of the flow generator outlet 25 and the exterior of the outlet 25.

In the illustrated configuration, the seal between the sensor 23 and the flow generator housing is formed using an interference fit between the silicone sensor 23 and the rigid flow generator housing. In at least one configuration, a barb fit can be used. In at least one configuration, the sensor 23 can include a projection on the side of the intermediate section 41 to assist retaining the sensor 23 in place. In at least one configuration, the projection can assist in forming an interference fit with a cooperating recess on the flow generator housing 27.

In at least one configuration, the sensor 23 can be retained by projections on the exterior surface of the flow generator housing 27. For instance, the flow generator housing 27 can include hook-like projections that can fit around the transducer contacting section 43 of the sensor 23 to retain the sensor 23 in place.

A circular profile of the intermediate section 41 may be advantageous as it can simplify the prototype manufacturing process of the flow generator 21 with the integrated sensor 23. It is generally simpler to manufacture a circular hole on a wall of the outlet 25 of a flow generator 21 than a square hole, or a hole of another profile, into which the intermediate section 41 of the sensor 23 must fit. When industrially applied, the hole could be moulded in the correct configuration.

In some embodiments, the circular profile of the intermediate section 41 can include at least one projection projecting outwardly from a portion of the side wall of the intermediate section 41. The projection can, for instance fit into a channel in the housing 27 or outlet 25 such that, when the sensor 23 is rotated about the vertical axis D, the sensor 23 is locked in place. The projection can project outwardly, away from the intermediate section 41. The hole in the flow generator housing 27 designed to accommodate the intermediate section 41 of the sensor 23 can be configured with a corresponding recess such that the projection of the intermediate section 41 cooperates with the recess to form a key-like orientation retaining system. The recess and the projection can cooperate such that they act as an aligning feature for the sensor 23. This aligning feature can enable the probe to be correctly aligned such that the longer length of the oval fluid contacting section 39 is approximately parallel to the direction of fluid flow.

In some embodiments, the intermediate section 41 can include a recess, and the flow generator housing 27 can include a cooperating projection. In at least one embodiment, the intermediate section 41 can be configured to include more than one projection or recess, with the hole in the flow generator housing 27 including more than one of the cooperating projection.

The transducer contacting section 43 in generally oblong in plan, cuboidal, and includes a first transducer contacting section horizontal surface 61 configured to abut and seal against the exterior of the outlet 25, an opposed, parallel second transducer contacting section horizontal surface 63 configured to abut, or be in communication with transducer 51. In the illustrated embodiment, the transducer contacting section 43 includes an oblong, rectangular profile having rounded corners, when viewed in plan along vertical axis D. The longitudinal dimension of the transducer contacting section 43 is approximately 11.2 mm in this example. The lateral dimension of the transducer contacting section 43 is approximately 8.2 mm in this example. The profile of the transducer contacting section 43 is not particularly limited to the shape and configuration shown. In the illustrated configuration, the centres of the fluid contacting section 39, the intermediate section 41, and the transducer contacting section 43 are coaxial with the central axis D of the flow sensor 23. In other embodiments, such as shown in FIGS. 16 to 19, one or more the sections 39, 41 and 43 may be offset so that their centres are not co-axial.

The sensor 23 is symmetric about the vertical axis D. The total vertical dimension of the sensor 23 in the illustrated configuration is approximately 7.2 mm. The vertical dimension of the fluid contacting section 39 is approximately 4.0 mm. In other words, the fluid contacting section 39 constitutes approximately 55.6% of the total vertical dimension of the sensor 23.

The vertical dimension of the intermediate section 41 is approximately 2.2 mm. In other words, the intermediate section 41 constitutes approximately 30.6% of the total vertical dimension of the sensor 23. The vertical dimension of the intermediate section 41 of the flow generator 21 can be considered to be limited to the thickness of the outlet 25 of the flow generator 21, that is, the vertical dimension of the intermediate section 41 corresponds to the thickness of the flow generator outlet 25 where the sensor 23 is located.

The vertical dimension of the transducer contacting section 43 is approximately 1.0 mm. In other words, the transducer contacting section 43 constitutes approximately 13.8% of the total vertical dimension of the sensor 23. The transducer contacting section 43 is configured to prevent the sensor 23 from being pressed too far into the flow path. The thickness, hardness, flexibility and/or strength of the transducer contacting section 43 is selected accordingly.

The vertical dimension of the first sensor opening 49 is approximately 1.0 mm. In other words, the first opening 49 constitutes approximately 25% of the vertical dimension of the fluid contacting section 39. The distance from the centre of each opening 49, 53 to the inner wall 31 of the outlet 25 is 2.75 mm in this example, but may be selected to minimise boundary layer effects. The distance of the openings 49, 53 from the intermediate section 41 may therefore be selected accordingly. Although the vertical dimension of the first opening 49 in the illustrated configuration is approximately 1.0 mm as it was found this provided the best results, other vertical dimensions are able to be used. This dimension provides an averaging effect for dynamic pressure for flow in this area. This dimension may be smaller, but this may lead to non-linearities in sensor response due to removing the averaging effect that is provided by a larger opening 49, 53. The width of each opening 49, 53 can make a difference to the accuracy, but this effect is typically not significant. Manufacturing limitations may make it difficult to manufacture a first opening 49 with a vertical dimension less than 1.0 mm however.

The most vertical point of the first opening 49 along vertical axis D is vertically displaced from the fluid contacting section horizontal surface by approximately 0.75 mm. The dimension is largely defined by manufacturing abilities. Reducing the distance between the fluid contacting horizontal surface and the first opening/second opening 49, 53 can reduce the reliability of the manufacturing process. The first opening 49 can be said to be located within the most vertical (or top) half of the fluid contacting section 39.

The profile of the first internal channel 45 and the second internal channel 47 is important for both feasibility of manufacture and for maintaining linearity in the measured values of Δp. If the diameter of either channel 45, 47 is too small, Δp readings can be effected in a negative way.

It should also be noted that both the first internal channel 45 and second internal channel 47 include apertures 45A, 47A on the fluid contacting section horizontal surface. A reason for this is for manufacturability. The channels 45, 47 span the vertical length of the sensor 23 to allow tooling pins to locate in the mould on each side. An additional benefit that was found was that when the channels 45, 47 span the length of the sensor 23, the Δp measurements determined by the sensor 23 were more suitable for flow determination. A more linear response was observed as the flow rate was increased.

Figure 15A:
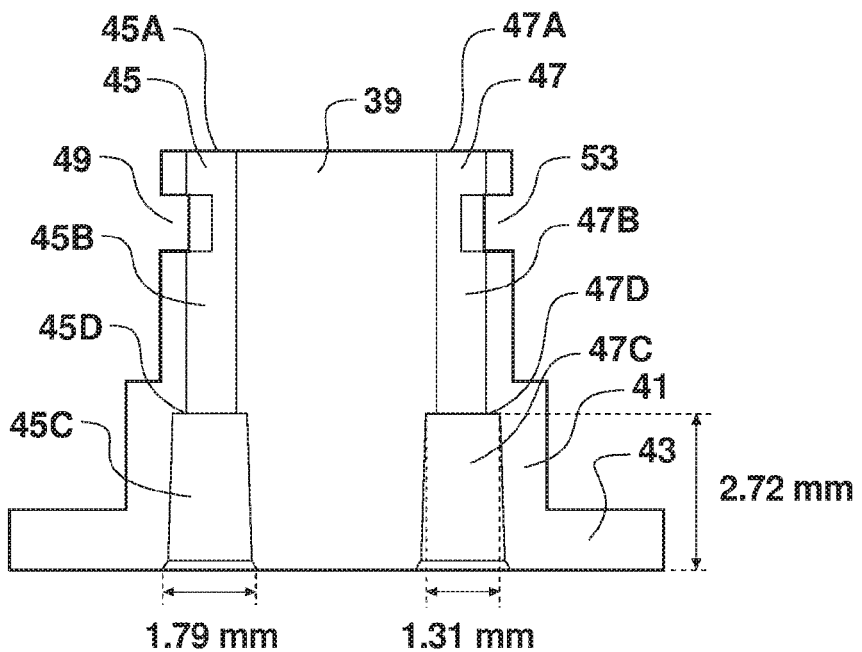
FIGS. 15a and 15b are sectional side views of the sensor of FIG. 2, with FIG. 15b showing the pins used as part of the sensor manufacturing process.
Figure 15B:
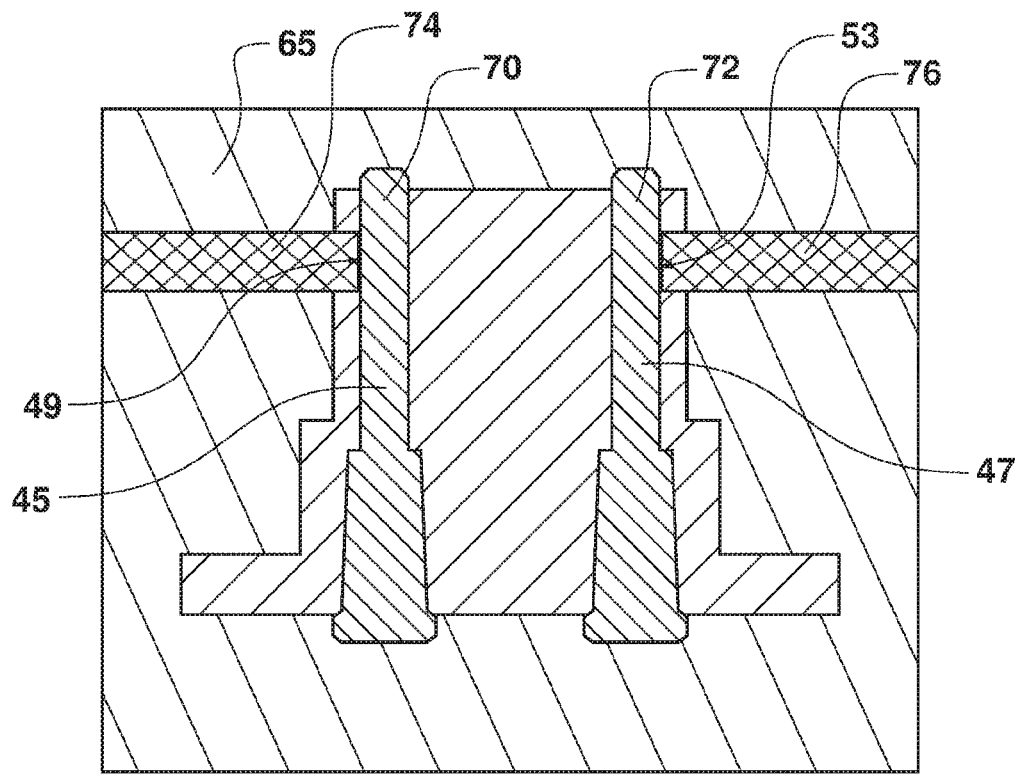
Figure 16:
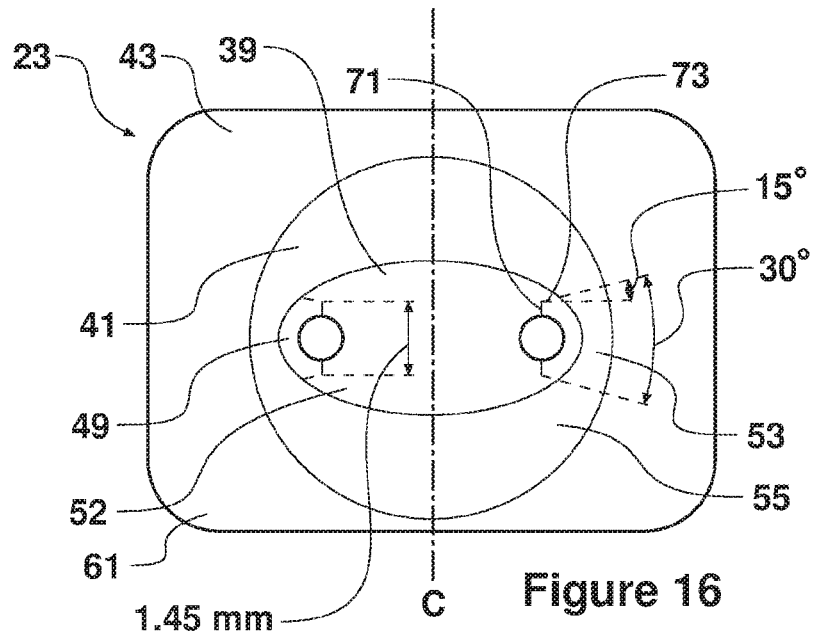
FIG. 16 is a sectional plan view taken on line X-X of FIG. 14.

FIG. 15B shows a cross sectional front view of the sensor 23 in a mould 65, including a first tooling pin 70 and a second tooling pin 72 used to mould the first internal channel 45 and the second internal channel 47. Third and fourth tooling pins 74, 76, extend perpendicularly to first and second pins 70, 72, and are used to form the openings 49, 53.

The first internal channel 45 and second internal channel 47 have the same profile, reflected about the vertical axis D. The first internal channel 45 includes a first length 45B and a second length 45C. The first length 45B is a circular channel of approximately constant radius spanning from the fluid contacting section horizontal surface to an interface vertically displaced from the fluid contacting section horizontal surface. The second length 45C of the first internal channel 45 spans from the interface 45D at the first length 45B to the second transducer contacting section horizontal surface. The second length 45C is a channel with a first radius at the interface 45D, and a second, larger radius at the second transducer contacting section horizontal surface.

In the illustrated embodiment, the interface includes an instantaneous increase in radius with respect to the first internal channel 45. In other words, the radius increase approximates a step function at the interface from the radius of the first length to the radius of the second length. The radius of first length 45B in the illustrated embodiment is approximately 0.85 mm. The radius of the second length 45C is approximately 1.31 mm at the interface 45D, and approximately 1.79 mm at the second transducer contacting section horizontal surface. In other words, the second length 45C resembles a truncated cone projecting in the vertical direction with a base of largest radius aligned with the plane formed by the lateral and longitudinal axes.

The second length 45C has an increased radius as it acts as an interface with the transducer. In the illustrated configuration, the transducer (sensor) 51 has two projecting ports which fit into the second lengths of the first and second internal channels 45, 47, allowing the transducer 51 to be attached to the sensor 23. An interference fit is used to retain the transducer 51 to the sensor 23. In other words, the second length 45C is configured as described so that an interference fit can be made with the transducer 51 to be used.

The transducer 51 includes a first port and a second port. Each port on the transducer 51 resembles a truncated cone, and therefore the second length of each channel 45, 47 of the sensor 23 can resemble a truncated cone.

In at least one embodiment, the interface 45D can facilitate a smooth change in radius between the first length 45A and the second length 45C. In at least one embodiment, the interface can comprise a region that spans a substantial vertical length of the first internal channel 45.

In at least one embodiment, the radius of the second length 45C may decrease with increasing vertical displacement from the interface (i.e. the orientation of the truncated cone in the existing design can be reversed). This configuration would enable a port to be fit in using a barb-like configuration.

In at least one embodiment, the radius of the first internal channel 45 can be a constant along the entire vertical length of the sensor 23. In at least one embodiment, the radius of the first internal channel 45 can vary along the vertical length of the sensor 23, that is, the first internal channel can be tapered. In at least one embodiment, a rounded edge can indicate the region at which the second length integrates with the second transducer contacting section horizontal surface.

With particular reference to FIGS. 13-16, the first opening 49 and second opening 53 are symmetric about the lateral axis C of the sensor 23. Additionally, the first opening 49 and second opening 53 are symmetric about the longitudinal axis B. Each of the first opening 49 and the second opening 53 includes at least one lateral wall 71 and at least one angled wall 73. The lateral wall 71 projects outwardly approximately 0.3 mm from the first opening 45 in a direction approximately parallel to the lateral axis C. The extent to which the lateral wall 71 projects outwardly influences the consistency of the pressure readings. It was found, in one example, that a projection of 0.3 mm was found to best suit the application.

The angled wall 73 then projects outwardly to the peripheral surface of the fluid contacting section 39. In at least one embodiment, the angled wall 73 projects outwardly from the lateral axis C at an angle of approximately 75°. Another way of expressing this is that the angled wall 73 projects outwardly from the longitudinal axis B at an angle of approximately 15°. Again, this angled profile was found to provide the best results in the current example. Other angles may be selected as required.

Figure 17:
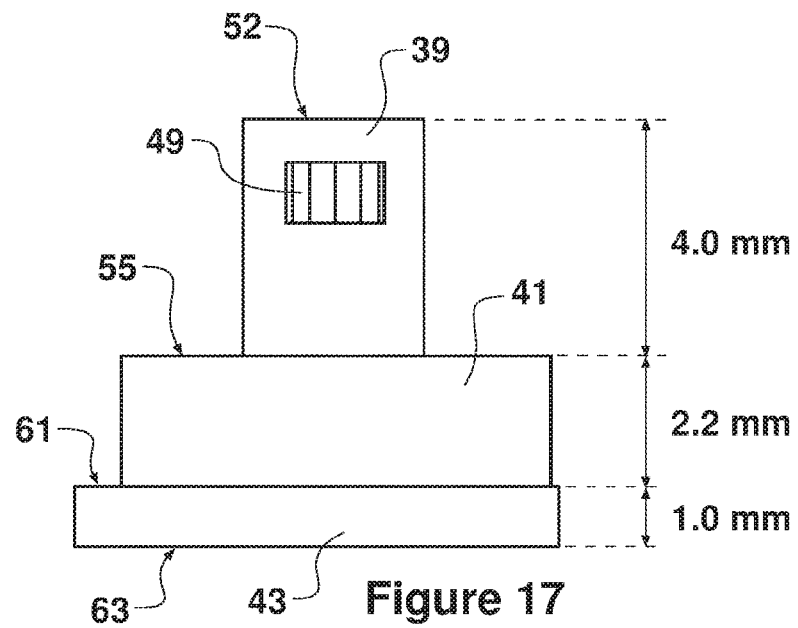
FIG. 17 is a left side view of the sensor of FIG. 2.
Figure 18:
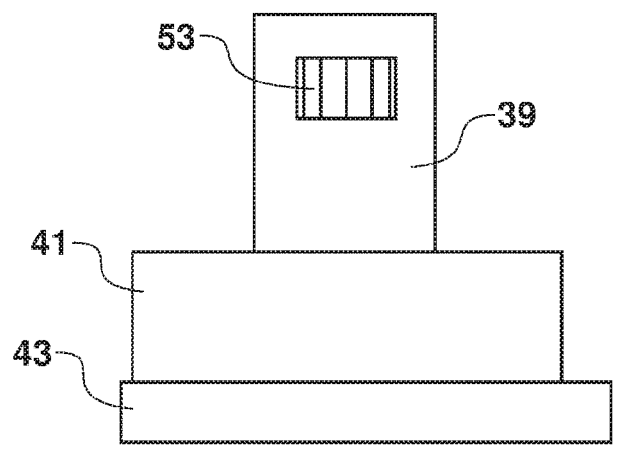
FIG. 18 is a right side view of the sensor of FIG. 2.
Figure 19:
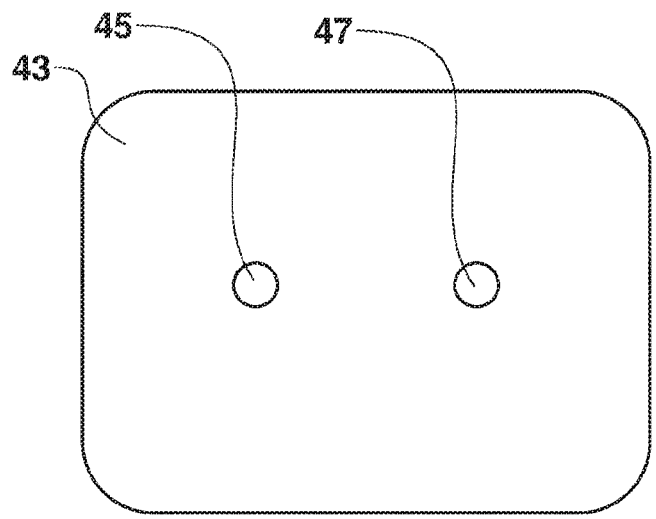
FIG. 19 is a bottom view of the sensor of FIG. 2.

With reference to FIGS. 17 and 18, the profile of the first and second openings 49, 53 is rectangular when viewed along the axis of each opening 49, 53. In at least one embodiment, this profile could be circular, oval, or any other shape.

Flow Generator Second Embodiment

Figure 20:
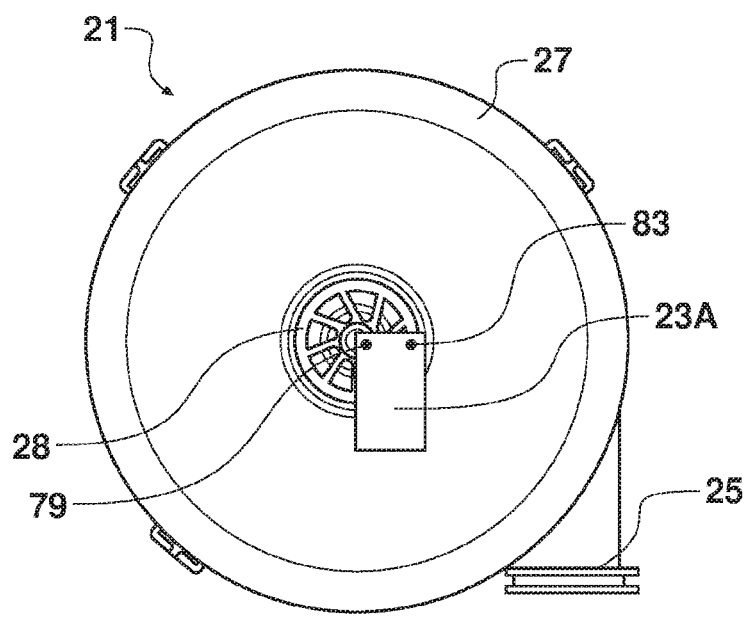
FIG. 20 is a plan view of a further flow generator in accordance with an aspect of the present invention.
Figure 21:
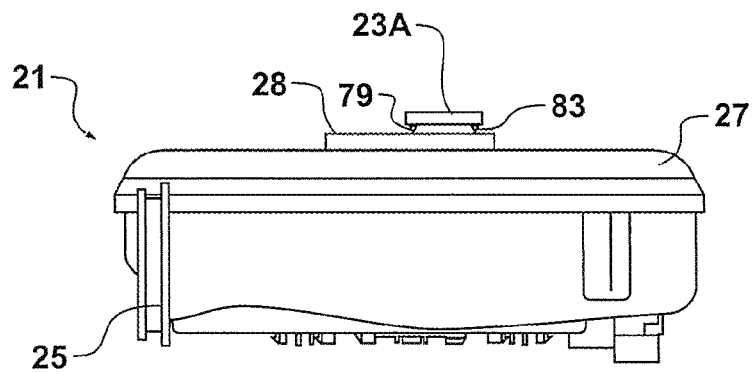
FIG. 21 is a side view of the flow generator of FIG. 20.

With reference to FIGS. 20 and 21, a second embodiment of the flow generator 21 relocates a sensor 23A to the inlet 28 of the flow generator 21. In this embodiment, the flow generator 21 is a centrifugal flow generator, as described above, but with the sensor 23A positioned at the axial inlet 28. The principle of operation is as above, whereby the sensor 23A is positioned in, and takes a pressure tap, from an existing region of relatively high flow within the flow generator 21.

In this case, the sensor 23A uses the same principles as the sensor 23 used in the previous embodiment, and is coupled to an identical or similar electrical transducer 51. In this example, the sensor 23A comprises first and second openings 79, 83, corresponding to openings 49, 53 of sensor 23. The first and second openings 79, 83 in this example, are in direct communication with the flow of breathable gas. An advantage of placing the sensor 23A at the inlet 28 is that a probe or flow contacting section 39 as previously disclosed is not required to project into the gas flow path.

In the illustrated configuration, the fluid adjacent the first opening 79 is relatively low velocity, while the fluid adjacent the second opening 83, further from the rotational axis of the impeller, is relatively high velocity. This velocity difference results in a corresponding pressure difference between the first opening and the second opening. This pressure difference can be detected by a transducer 51 (not shown), providing a value for Δp. These Δp values can be appropriately calibrated as previously disclosed to enable a reading of the flow through the flow generator 21 to be estimated with acceptable accuracy. The spacing between the openings 79, 83 affects the accuracy of reading, and in this example is about 4.3 mm.

The sensor 23A of FIGS. 20 and 21 can be held in place by any means desired. In at least one embodiment it can form part of, or be connected to a larger circuit board. In some configurations, it can be suspended in place via a structure that forms part of, or is connected to the flow generator housing 27.

In at least one embodiment, the sensor 23A can be in a different position to that shown in FIGS. 20 to 21. The probe can be rotated around the inlet 28 in any configuration that is rotated about the centre of the inlet 28, that is, the distance between the first port and the peripheral boundary of the inlet remains approximately constant, and the distance between the second port and the centre of the inlet 28 remains constant, however the sensor is configured at a different location of the inlet 28 to that shown.

Figure 22:
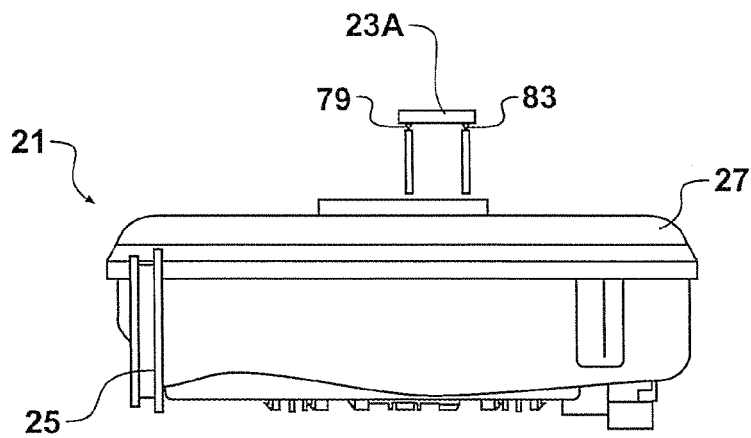
FIG. 22 is a front view of the flow generator of FIG. 20

With reference to FIG. 22, another embodiment of the sensor arrangement of FIGS. 20 and 21 is shown.

In this configuration, the sensor 23A is suspended at a greater distance from the inlet 25 of the flow generator 21. A first tube 85 connects to the first opening 79 and projects downward to a point that is in close proximity to the flow generator inlet 28. A second tube 87 connects to the second opening 83 and projects downward to a point that is in close proximity to the flow generator inlet 28. The first tube 85 and second tube 87 act as a means of extending the first opening 79 and the second opening 83 so that the sensor 23A can still be used to measure a value for Δp between the two locations.

It is considered that some of the benefits of the above disclosed flow generator, sensor and respiratory system may include:

Integrating the sensor with the flow generator saves space, allowing a CPAP device to be miniaturised.

Integrating the sensor into the flow generator allows the flow generator 21 to be fabricated as an independent unit or module with no auxiliary components.

The location of the sensor within the flow generator, particularly in a region of high fluid velocity with consistent, repeatable fluid behaviour for the entire operating range of the CPAP device. In some examples, this operating range may be about 4 cmH2O-20 cmH2O, whilst in other examples, such as a bi-level system, the operating range may be about 0-40 cmH2O.

The location of the sensor within the flow generator in an existing high velocity area makes for minimal system pressure drop.

The method of calibrating data readings from the sensor to determine the flow rate of the flow generator discharge.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

The invention claimed is:

1. A flow generator for a respiratory therapy system configured to deliver a breathable gas flow to a patient, the flow generator comprising:
   a flow generator housing comprising an inlet, an outlet, and a gas flow path extending between the inlet and the outlet;
   an impeller mounted within the flow generator housing and rotatable about an axis, the impeller configured to be rotationally driven by a motor to provide a gas flow along the gas flow path; and
   a sensor mounted in the flow generator housing in the gas flow path, the sensor configured to detect a property of the gas flow, the sensor comprising a first channel and a second channel,
   wherein the first channel and the second channel each span a length of the sensor in a direction perpendicular to the gas flow.

2. The flow generator of claim 1, wherein the sensor comprises a fluid contacting horizontal surface.

3. The flow generator of claim 2, wherein the first channel and the second channel each comprise an aperture on the fluid contacting horizontal surface.

4. The flow generator of claim 3, wherein the first channel and the second channel each span a vertical length of the sensor.

5. The flow generator of claim 1, wherein the first channel and the second channel each span between a first end of the sensor and a second end of the sensor.

6. The flow generator of claim 1, wherein the sensor comprises a first opening on a first side of the sensor and a second opening on a second side of the sensor.

7. The flow generator of claim 1, wherein the flow generator housing is received within an outer housing.

8. The flow generator of claim 1, wherein the first channel comprises a first portion and a second portion, and the second channel comprises a first portion and a second portion, the second portion of each of the first channel and the second channel comprising a channel radius larger than the first portion of each of the first channel and the second channel.

9. The flow generator of claim 1, wherein the second channel is identical to the first channel.

10. The flow generator of claim 1, wherein the sensor comprises a pair of internal sensor flow paths each extending from a respective sensor opening in a direction substantially parallel to a longitudinal axis of the sensor, each of the pair of internal sensor flow paths being configured to communicate with a flow transducer, the flow transducer being operative to generate a signal indicative of the gas flow in the gas flow path from gas entering the sensor through the sensor openings.

11. The flow generator of claim 10, wherein the flow transducer comprises at least two projecting ports that attach to the sensor.

12. The flow generator of claim 1, wherein the sensor further comprises a sensor body including a fluid contacting section, an intermediate section, and a transducer contacting section.

13. The flow generator of claim 12, wherein the first channel and the second channel each travels through the fluid contacting section, the intermediate section, and the transducer contacting section.

14. The flow generator of claim 1, wherein the sensor is configured to determine a flow rate of the gas flow.

15. The flow generator of claim 1, wherein the sensor is configured to determine a flow rate of the gas flow from an output differential pressure value.

16. The flow generator of claim 1, wherein the sensor comprises an oval or elliptical profile in plan view.

17. The flow generator of claim 14, wherein the sensor is configured to produce a substantially linear response when determining the flow rate of the gas flow.

18. The flow generator of claim 1, wherein the first channel and the second channel each comprises a circular profile of a constant radius.

* * * * *